United States Patent
Page et al.

(10) Patent No.: US 11,845,070 B2
(45) Date of Patent: Dec. 19, 2023

(54) SURFACE PLASMON ENHANCED PHOTOCATALYSIS

(71) Applicant: Ciencia, Inc., East Hartford, CT (US)

(72) Inventors: William D. Page, Storrs, CT (US); George N. Gibson, Storrs, CT (US); Stephen B. Cronin, South Pasadena, CA (US); Arturo O. Pilar, Coventry, CT (US); Ernest F. Guignon, Canton, CT (US)

(73) Assignee: Ciencia, Inc., East Hartford, CT (US)

( * ) Notice: Subject to any disclaimer, the term of this patent is extended or adjusted under 35 U.S.C. 154(b) by 847 days.

(21) Appl. No.: 16/625,466

(22) PCT Filed: Jun. 23, 2018

(86) PCT No.: PCT/US2018/039174
§ 371 (c)(1),
(2) Date: Dec. 20, 2019

(87) PCT Pub. No.: WO2018/237367
PCT Pub. Date: Dec. 27, 2018

(65) Prior Publication Data
US 2021/0146347 A1    May 20, 2021

Related U.S. Application Data

(60) Provisional application No. 62/524,072, filed on Jun. 23, 2017.

(51) Int. Cl.
*B01J 19/12* (2006.01)
*B01J 35/00* (2006.01)
(Continued)

(52) U.S. Cl.
CPC ............. *B01J 35/004* (2013.01); *C01B 3/042* (2013.01); *C01B 13/0207* (2013.01);
(Continued)

(58) Field of Classification Search
CPC ..... B01J 35/004; B01J 19/08; G02F 2203/10; G01N 2021/258
(Continued)

(56) References Cited

U.S. PATENT DOCUMENTS 7,426,322 B2 *  9/2008  Hyde ..................... B01J 19/127
                                                    359/240
8,075,980 B2 * 12/2011  Eldering ................... B32B 9/04
                                                    362/621
(Continued)

FOREIGN PATENT DOCUMENTS

JP      2009045514 A    3/2009
JP      5629931 B2      11/2014

OTHER PUBLICATIONS

Nootchanat et al., Investigation of localized surface plasmon/grating-coupled surface plasmon enhanced photocurrent in TiO2 thin films, 2014, Phys. Chem. Chem. Phys., vol. 16, pp. 24484-24492 (Year: 2014).*

(Continued)

*Primary Examiner* — Long T Tran
*Assistant Examiner* — James J Kim
(74) *Attorney, Agent, or Firm* — Alix, Yale & Ristas, LLP

(57) ABSTRACT

Plasmonically-enhanced catalytic surfaces and accompanying optics are described herein. These elements facilitate efficient coupling of light energy into a photocatalytic system by way of a surface plasmon. Various compatible optical configurations are presented, with an emphasis on the broadband coupling of light into a single plasmon mode. In an example embodiment, dispersive optics are used to direct polychromatic light onto a grating-embossed SPR-active surface. Dispersive optics allow resonance to be achieved at a wide range of incident wavelengths. Energy then transfers from the excited plasmon to an adjacent photocatalyst. The (Continued)

plasmon mode thus acts as a "funnel" of broadband light energy to the catalytic materials. High-efficiency incoupling and outcoupling from the plasmon mode suggest overall enhancement of catalytic activity, and broad applicability is anticipated due to the inherent flexibility of the system. The catalytic surfaces and optical components can be fabricated as sheets or 3D arrays, justifying industrial-scale manufacturing.

7 Claims, 18 Drawing Sheets

(51) Int. Cl.
    *C01B 3/04*     (2006.01)
    *C01B 13/02*     (2006.01)
    *G01N 21/25*     (2006.01)
    *G01N 21/63*     (2006.01)
    *G02B 5/18*     (2006.01)
    *G01N 21/64*     (2006.01)

(52) U.S. Cl.
    CPC ............ *G01N 21/25* (2013.01); *G01N 21/63* (2013.01); *G02B 5/18* (2013.01); *C01B 2203/0277* (2013.01); *C01B 2203/06* (2013.01); *G01N 2021/258* (2013.01); *G01N 2021/6478* (2013.01); *Y02E 60/36* (2013.01)

(58) Field of Classification Search
    USPC ...................................................... 204/157.4
    See application file for complete search history.

(56) References Cited

U.S. PATENT DOCUMENTS

| | | | |
|---|---|---|---|
| 8,749,866 B2 * | 6/2014 | Sweatlock | B82Y 20/00 359/245 |
| 9,383,312 B2 | 7/2016 | Page et al. | |
| 9,535,005 B2 | 1/2017 | Page et al. | |
| 2013/0118906 A1 | 5/2013 | Cronin et al. | |
| 2016/0033328 A1 | 2/2016 | Walters | |
| 2016/0313247 A1 | 10/2016 | Page et al. | |

OTHER PUBLICATIONS

Griffin et al., Biosensors [online], [retrieved on Mar. 19, 2022]. Retrieved from the internet: <URL: https://www.sciencedirect.com/topics/immunology-and-microbiology/surface-plasmon-resonance# :~: text=SPR > (Year: 2022).*

Extended European Search Report for Application No. 18821266.6-1107 / 3642322 PCT/US2018039174 dated Mar. 1, 2021; 5 pgs.

Zhao et al., "Study of Plasmonics induced Optical Absorption Enhancement of Au Embedded in Titanium Dioxide hanohole arrays" Optical Material Express, Aug. 2017, vol. 7, No. 8; 9 pgs. [online] URL =<https://www.osapublishing.org/DirectPDFAccess/B38E44E1-94E0-C246-91546692152119E3_369357/ome-7-8-2871.pdf?da=1&id=369357&seq=0&mobile=no>.

PCT International Search Report and Written Opinion for International application No. PCT/US2018/039174; dated Sep. 14, 2018; 7 pgs.

Ameta R., Ameta S.C., "Photocatalysis: Principles and applications" Crc Press. 2017; 138 pgs.

Lan Y, Lu Y, Ren Z., "Mini review on photocatalysis of titanium dioxide nanoparticles and their solar applications" Nano Energy. 2013; 2(5) pp. 1031-1045. doi: https://doi.org/10.1016/j.nanoen.2013.04.002; 15 pgs.

Willets K.A., Van Duyne R.P., "Localized Surface Plasmon Resonance Spectroscopy and Sensing" Annu Rev Phys Chem. 2007; 58:267-297; 33 pgs.

Hou W., Cronin S.B., "A Review of Surface Plasmon Resonance-Enhanced Photocatalysis" Advanced Functional Materials; 2013, 23(13):1612-1619. Doi: 10.1002/adfm.201202148; 8 pgs.

Homola J., "Surface Plasmon Resonance Based Sensors" Springer-Verlag. 2006; 253 pgs.

* cited by examiner

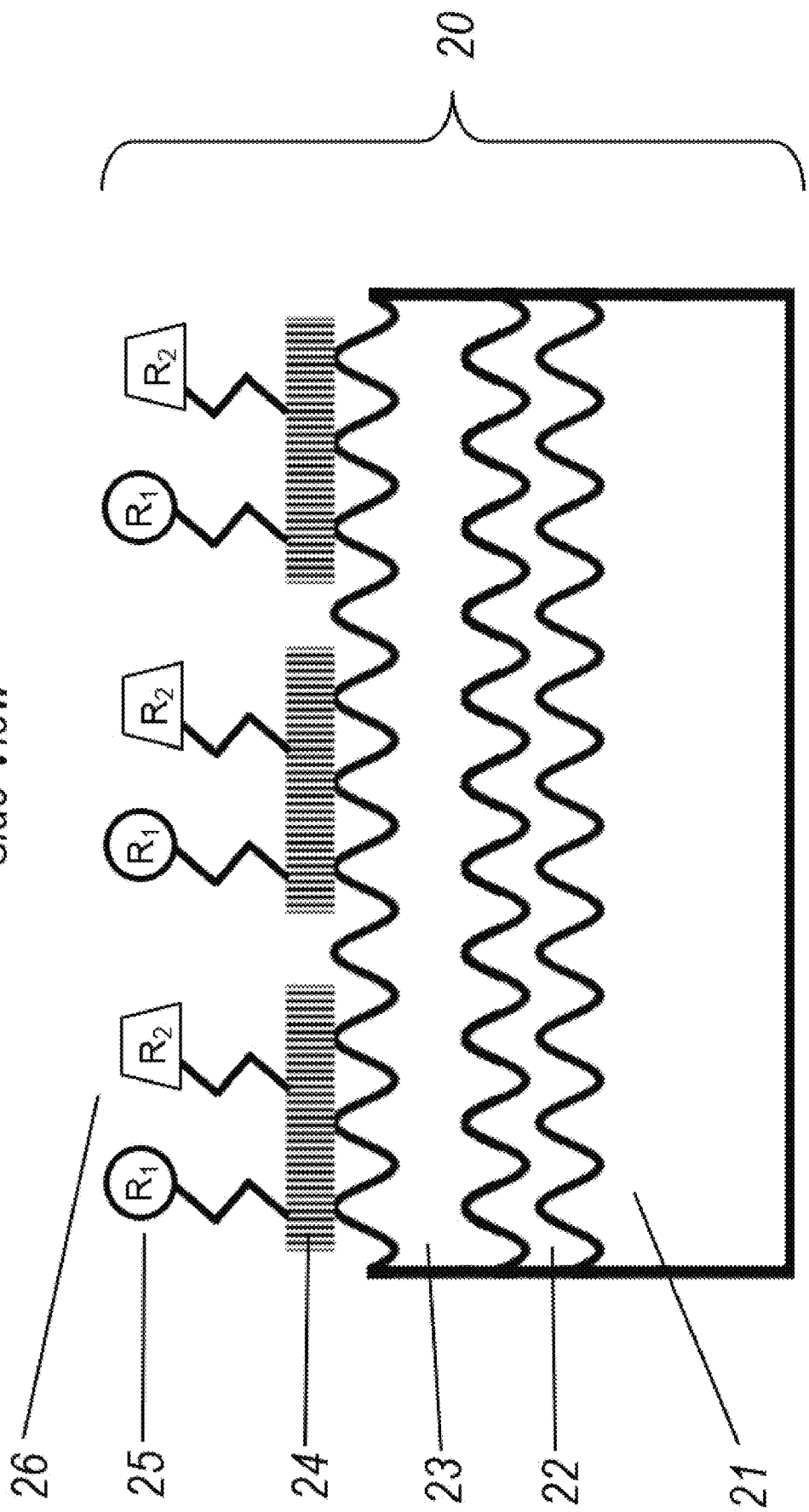

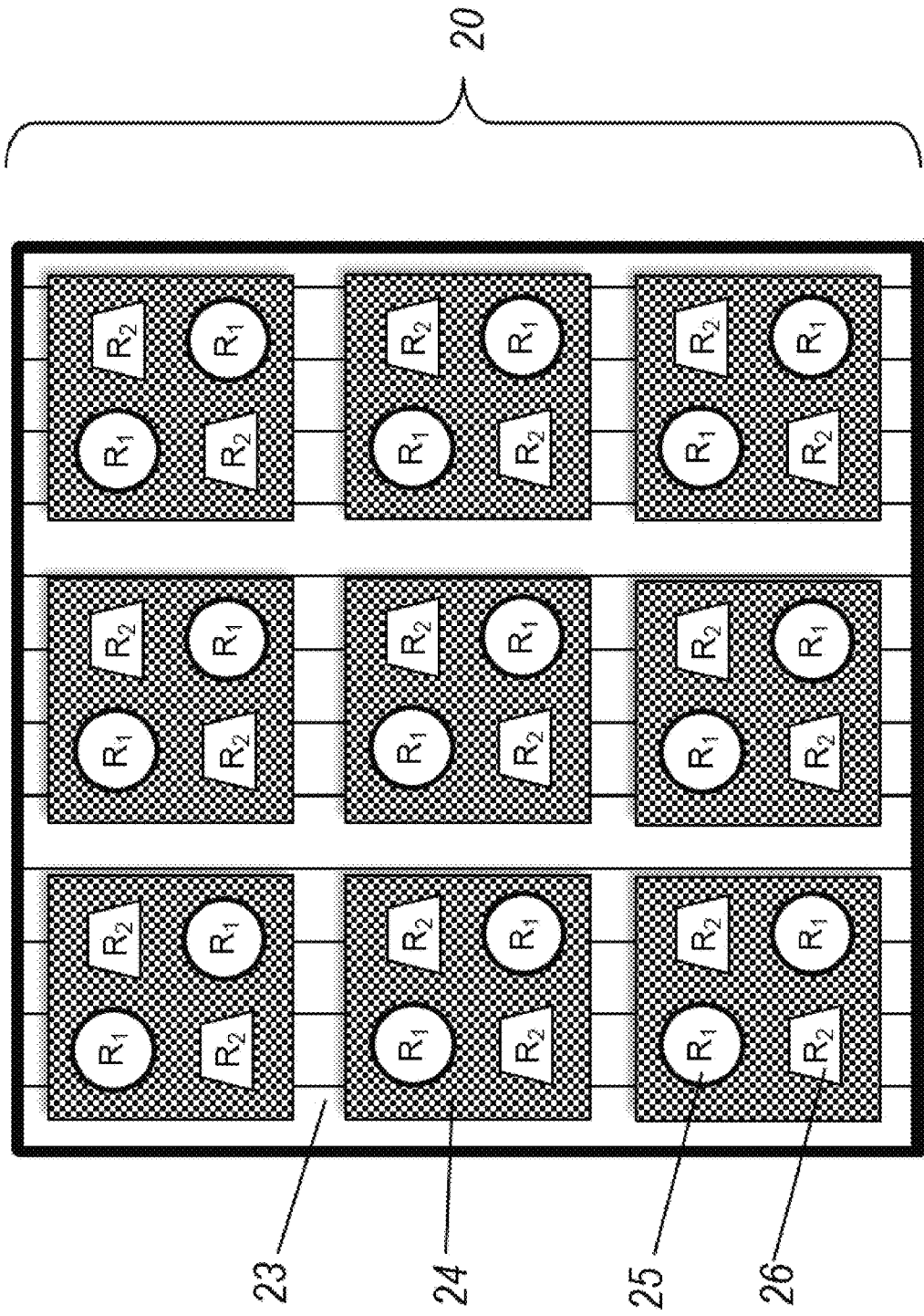

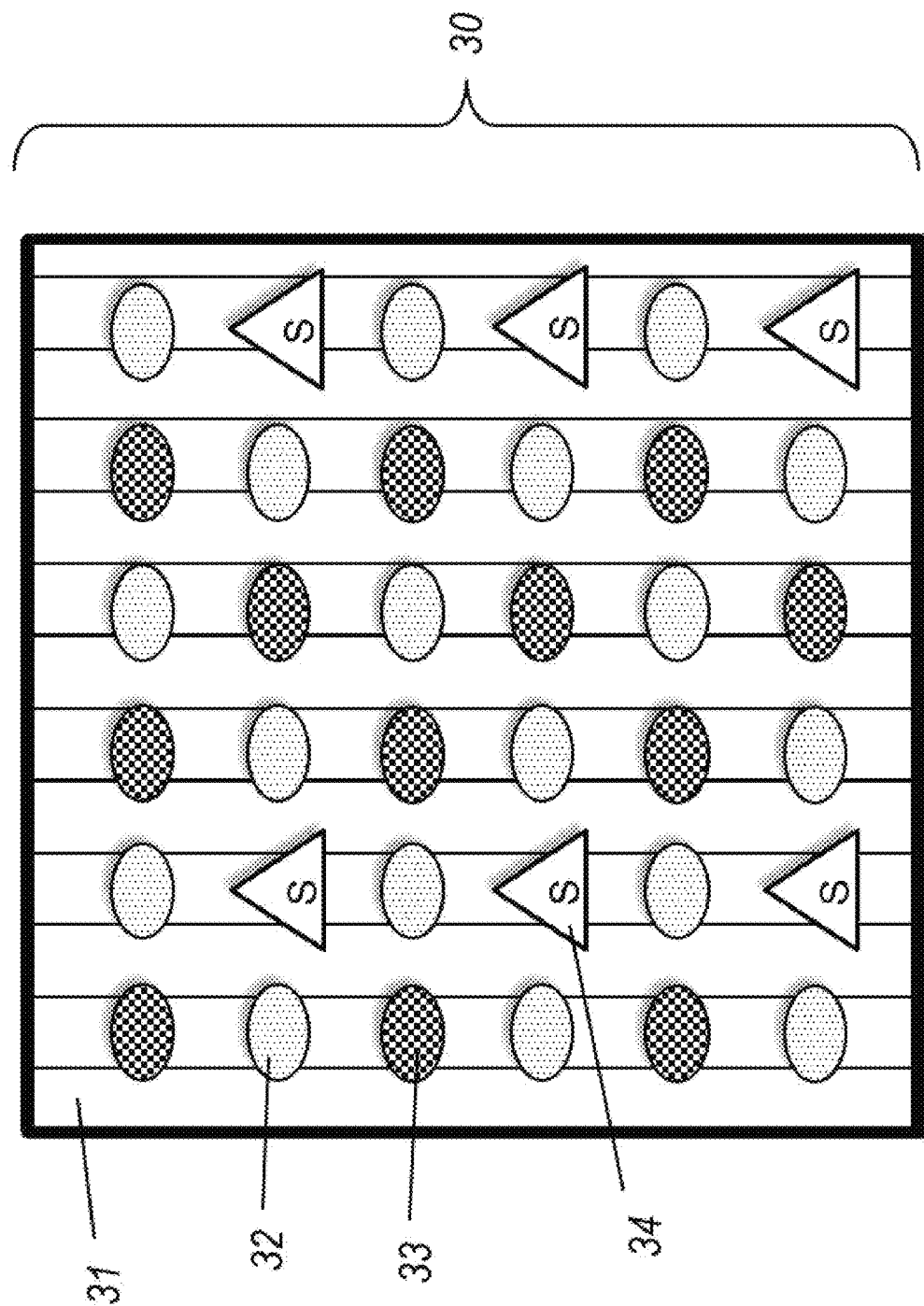

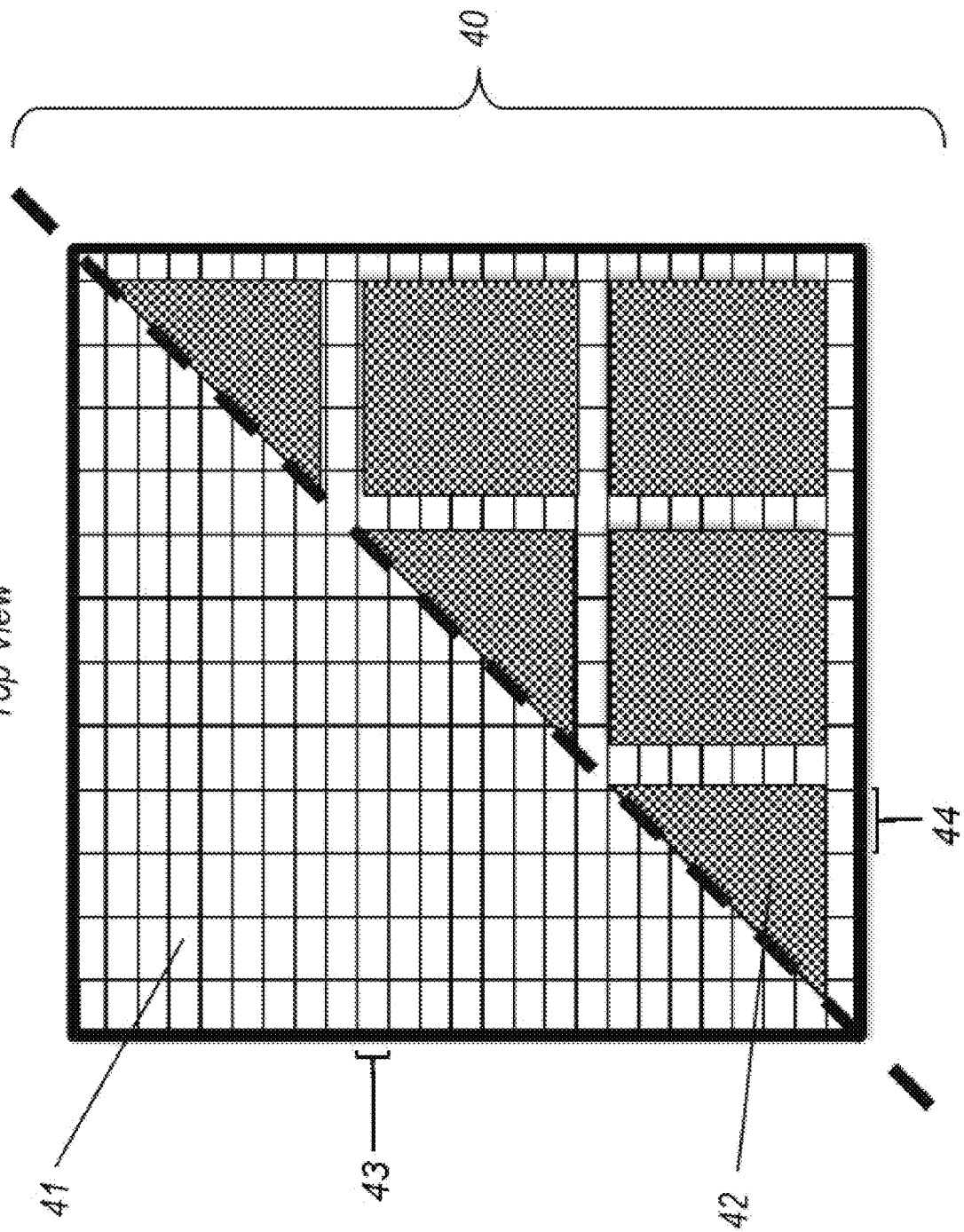

Oblique View

Side View

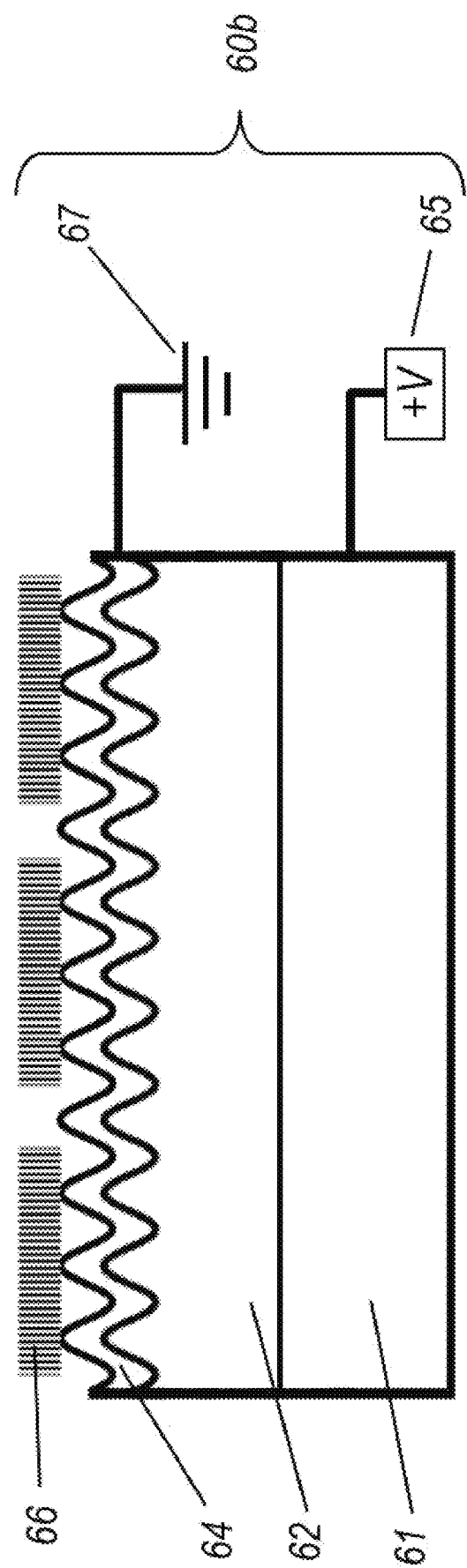

Side View

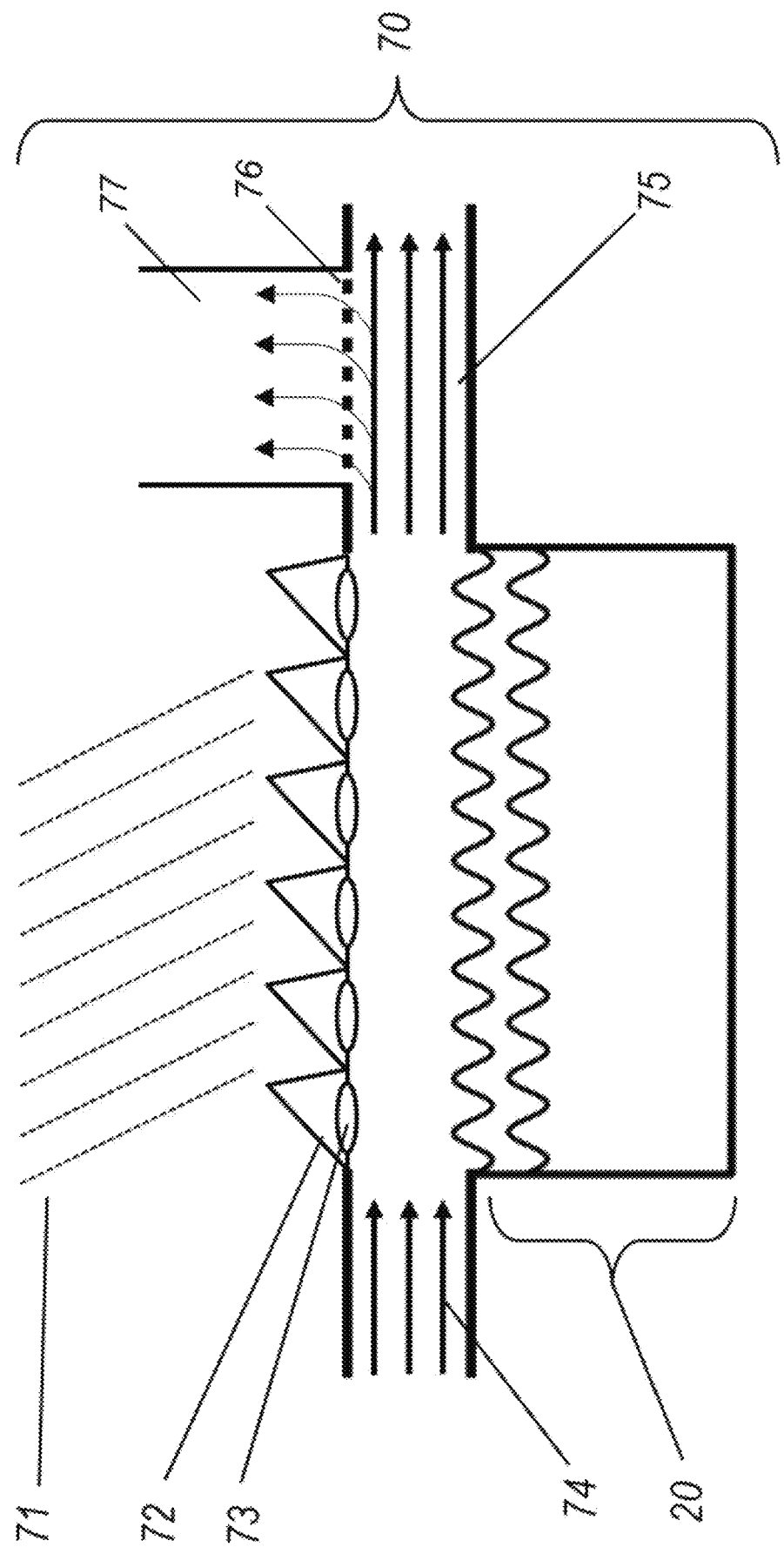

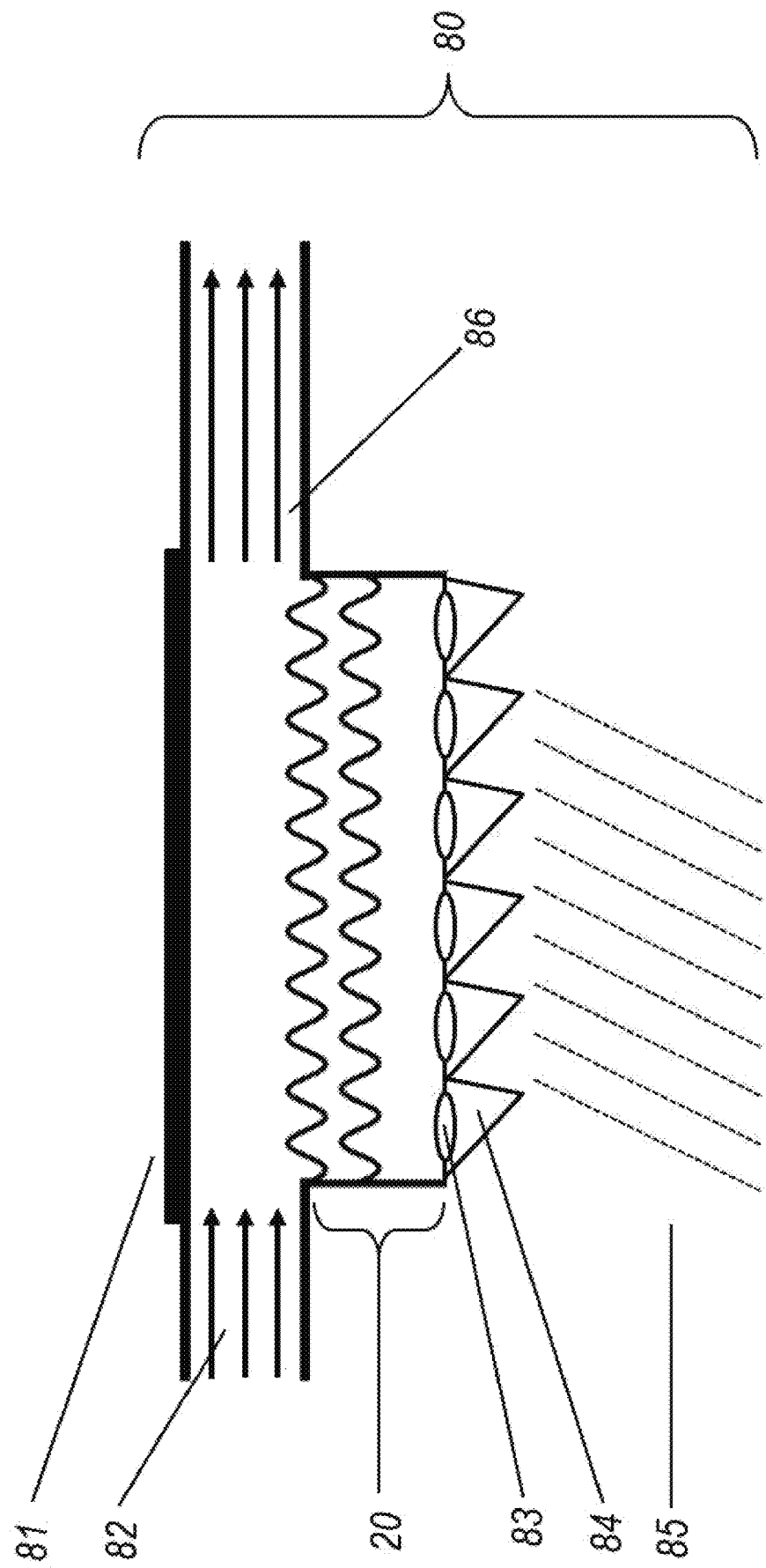

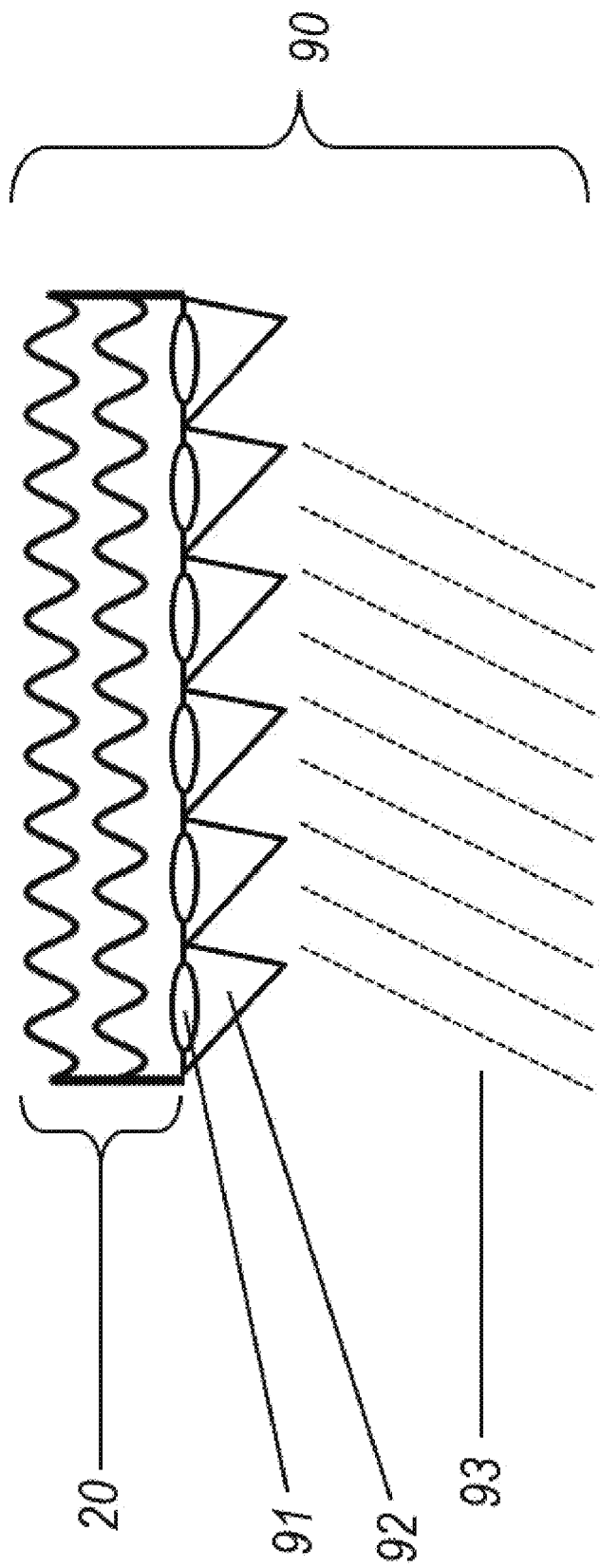

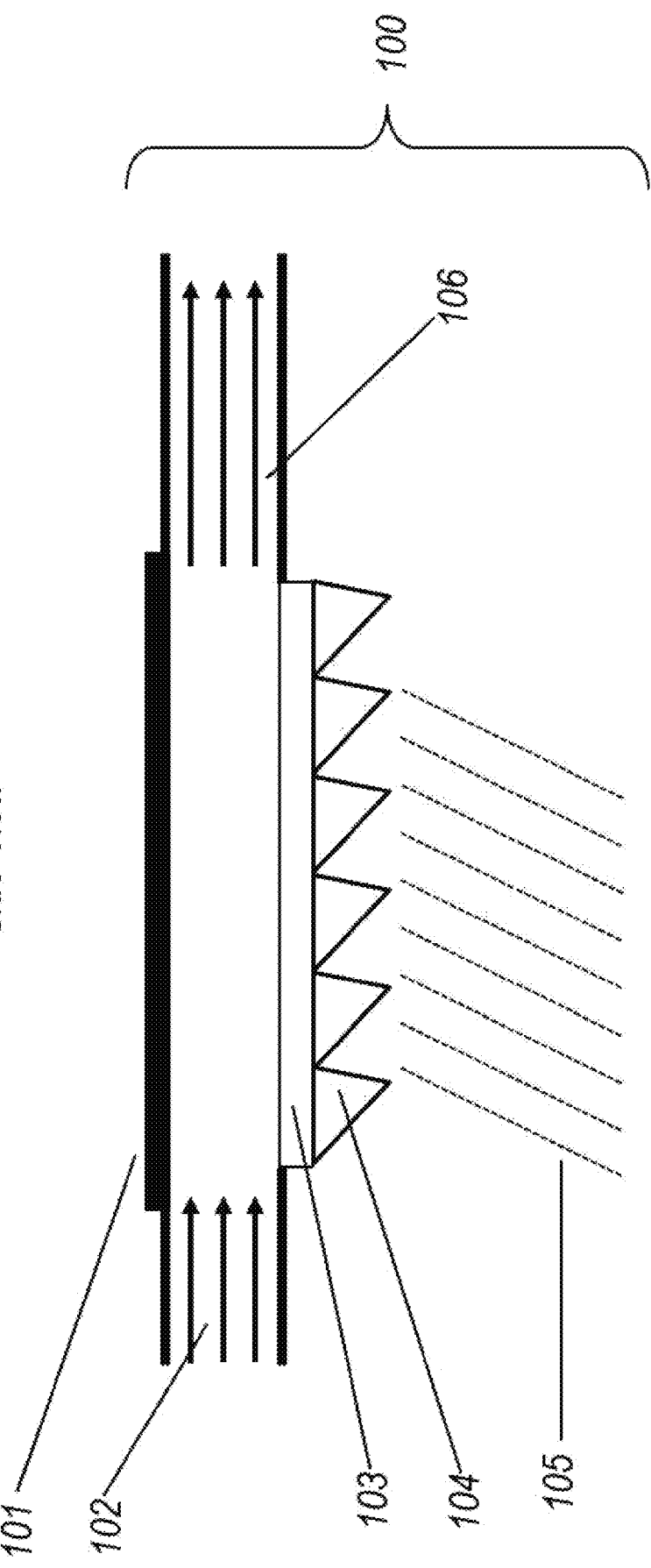

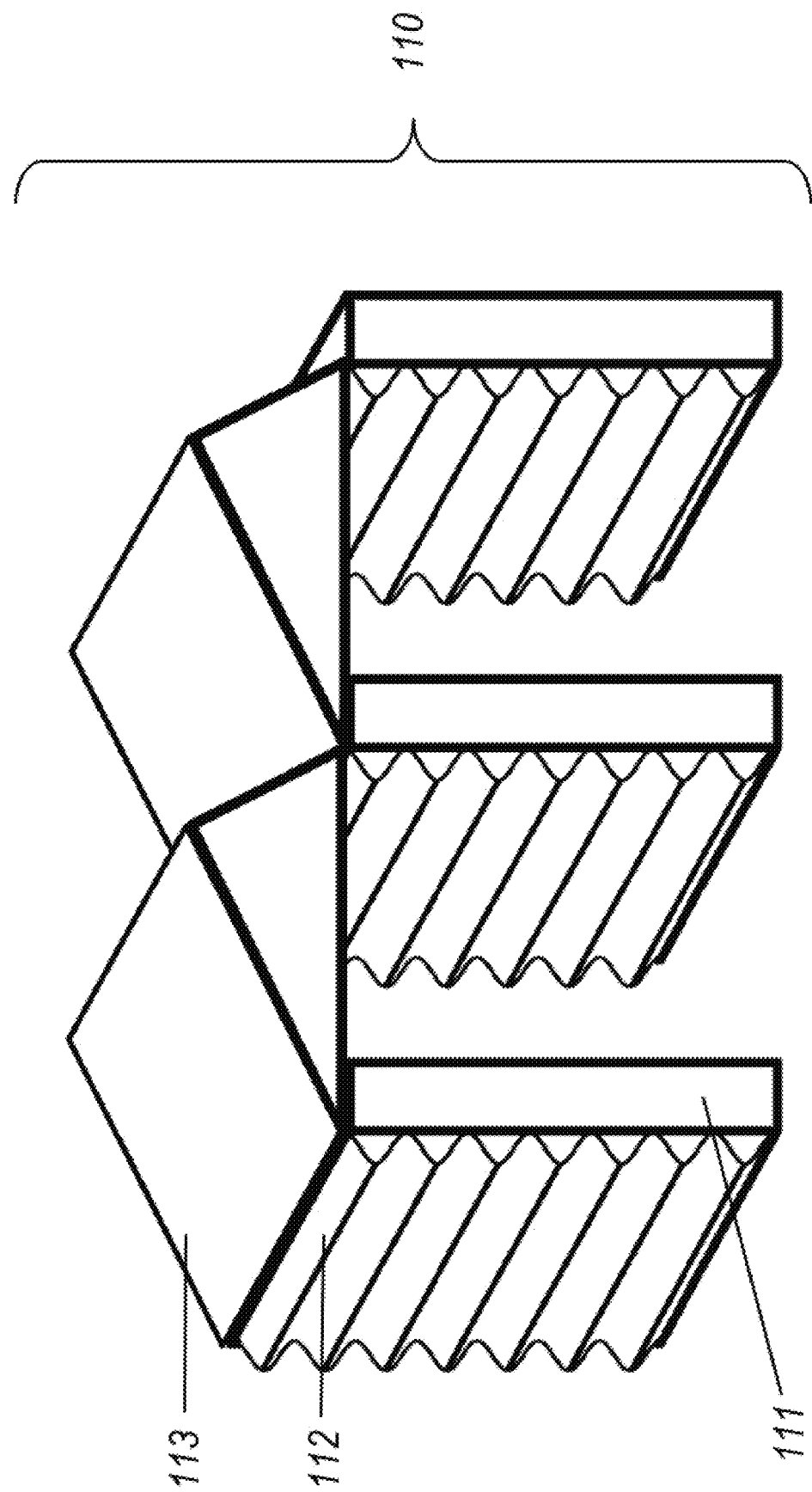

Oblique View

Oblique View

Oblique View

SURFACE PLASMON ENHANCED PHOTOCATALYSIS

FIELD OF THE DISCLOSURE

The described embodiments relate to a plasmonic photocatalytic system and the optics required for efficient transfer of incident light energy to drive chemical reactions.

BACKGROUND

Recent years have seen countless innovations permitting the increasingly efficient and cost-effective gathering of solar energy. Yet utilization of this abundant source remains hindered by limitations in technologies to store and deliver reliable on-demand energy, especially during times of low solar irradiance. The global efforts to retain solar energy gathered during the day to distribute at night are extensive and will not be repeated here, except to note that one promising and well-explored avenue of research uses light to drive chemical reactions in a process known as photocatalysis. As an example, photocatalytic splitting of water has been investigated as a source for clean and renewable hydrogen ($H_2$) to power fuel cells, but these catalytic systems have historically lacked the requisite blend of cost and efficiency for large-scale commercial viability.

While water splitting represents one highly desirable reaction, potential uses for a photocatalytic system are far broader, addressing established and emerging concerns in residential, commercial, and industrial sectors. The following applications are listed to outline the scope and potential importance of innovation in this field. Broad categories of disciplines that would benefit from an efficient photocatalytic surface structure include the following:

Solar energy storage: generation of $H_2$, synthesis of other energy-rich compounds, Environmental maintenance: treatment of wastewater, pollutant sequestration, treatment of air/exhaust, photochemical reduction of $CO_2$, Artificial photosynthesis: large-scale production of organic compounds, Medical applications: light-driven antimicrobial surfaces, self-cleaning surfaces, Building materials: self-cleaning structures.

These and additional uses for photocatalysis are described in detail by Amita and Amita; readers interested in further applications are encouraged to reference this text.[1]

The history of photocatalysis is often traced back to a 1972 publication reporting the serendipitous observation of water splitting by titanium dioxide ($TiO_2$). Since then, semiconductor photocatalysis has evolved to encompass thousands of distinct catalytic systems. Although there has been extensive research into other classes of materials, semiconductor-based systems remain particularly attractive for photocatalytic applications because their valence and conduction band energies are readily modified by the addition of dopants. While initially limited to binary metal oxides, newer semiconductor-based systems with distinct properties have been built from sulfides (e.g. CdS), ternary crystals (e.g. $PbCrO_4$), and quaternary crystals (e.g. $Cu_2ZnSnS_4$). Catalytic efficiency of pure semiconductor material is further tailored by the geometry of deposition ($TiO_2$ nanoparticles vs. thin film vs. bulk $TiO_2$) and by the internal crystalline geometry of the material (rutile vs. anatase $TiO_2$).[2]

Despite the wealth of semiconductor materials available, one prominent cause for inefficiency in photocatalytic systems to date arises from the limited overlap between the highest-intensity solar wavelengths and the optimal excitation wavelength for the catalyst. In a well-studied example, efficiency for direct sunlight on bulk $TiO_2$-based systems falls far short of the theoretical maximum because this material absorbs best in the ultraviolet range and poorly in the visible, therefore only utilizing a small percentage of the total solar energy. A considerable number of schemes have been employed to improve this catalytic efficiency including (but not limited to) localized surface plasmon resonance (LSPR), catalytic nanoparticles, as well as sensitizers built from organic dyes, inorganic dyes, and quantum dots. The important topic of sensitization is reviewed in detail by Amita and Amita. This text also defines the non-optical benefits of SPR-based photocatalysis, specifically including the role of metallization and the importance of the Schottky barrier in preventing electron-hole recombination. These latter phenomena are oft-cited features of LSPR systems and thus will not be recapitulated here, except to say that the proposed SPR platforms would benefit similarly from metal-photocatalyst interaction.

To briefly review, surface plasmon resonance is achieved when P-polarized light couples into a charge density oscillation at a metal-dielectric interface. This oscillation is allowed by a mismatch between the dielectric constants of these two materials, which together permit a surface-bound mode of electron excitation known as a plasmon. When conditions are optimal, the majority (>90%) of incident light acts to excite the plasmon, with little reflecting off the surface. Many variables define the conditions where resonance will occur, including the grating geometry, the identity of the SPR-active metal, the composition of the dielectric, the surface temperature, and the angle, wavelength, and phase of the incident light. SPR-active metals include gold Au, silver Ag, and aluminum Al. In addition, one of several momentum matching schemes are required for resonance with the surface plasmon. Four established schemes will be briefly described here: LSPR, the Kretschmann configuration, grating-coupled surface plasmon resonance (GCSPR), and the proprietary electro-optic grating-coupled surface plasmon resonance (EOSPR) developed at Ciencia, Inc.[†] This list is not exhaustive, but acts to highlight several important SPR technologies (and by extension SPR-based photocatalytic systems), and aids in distinguishing the technologies described herein from prior art.

LSPR—Localized surface plasmon resonance has been explored extensively for a diverse range of applications and has been incorporated into a variety of photocatalytic systems. The basic physics underlying LSPR are reviewed in Willets and Van Dunne[3] and photocatalytic applications are reviewed by Cronin et al.[4] Coupling conditions are less stringent in LSPR than in the Kretschmann or GCSPR configurations as the conditions for an LSPR particle does not depend on the incident angle. Eliminating the restrictions on the incident angle simplifies coupling into an LSPR particle. This advantage is likely a primary reason that plasmonic photocatalysis systems to date have been disproportionately based on LSPR. Yet while LSPR obviates angle dependency, resonant particles must be produced for each wavelength of the solar spectrum, representing a manufacturing challenge and a critical limitation to overall catalytic efficiency.

Kretschmann Configuration—The Kretschmann configuration represents one of the most common ways to achieve the momentum matching conditions required for SPR. This scheme is based on the inclusion of a high-refractive-index prism adjacent to an SPR-active metal layer, a principle that underlies most commercial SPR sensors. In a Kretschmann-based platform, the metal layer is sufficiently thin that resonant conditions are affected by the refractive index on both sides of the metal surface. In this way, Kretschmann-based biosensors detect biological interactions that occur on "top" of the metal sensor surface by monitoring the properties of the incident light (e.g. angle, wavelength, phase) and observing changes in the intensity of light that reflect from the "bottom" of the metal. Changes in the amount or identity of material bound at the surface affects the angle at which the minimum reflected intensity occurs. Later discussion is informed by the observation that in Kretschmann systems, the metal is sufficiently thin that resonant conditions become sensitive to both the prism-metal and metal-dielectric interfaces.

GCSPR—Grating-coupled surface plasmon resonance circumvents some of the cost, size, and logistical limitations of the Kretschmann configuration. Replacing the prism with a diffraction grating either embossed or otherwise patterned directly on the surface, GCSPR achieves resonance by coupling higher-order diffracted light into the surface plasmon. This scheme eliminates the high-refractive index prism and the need for index matching fluid, simplifying the optical pathways and reducing reagent-handling requirements. With this approach, light energy directly strikes the active metal-dielectric surface instead of passing through the prism-metal interface and the thin metal layer. The geometry of GCSPR optical components permits the manufacture and use of larger-scale SPR-active surfaces. Ciencia, Inc. has developed SPR-active gratings for various sensing applications, which have demonstrated enhancement of photocatalytic activity.

EOSPR—Electro-optic grating-coupled surface plasmon resonance is a grating-based surface architecture designed and patented by the principals at Ciencia.[†] Extracting elements from both the Kretschmann and GCSPR configurations, EOSPR resembles GCSPR but takes advantage of the fact that resonant conditions become sensitive to the dielectric constant on both sides of the SPR-active metal when this metal is sufficiently thin. Thinning of the metal permits the opportunity to further tune resonance by building the grating from static materials with desired dielectric constants (e.g. doped silicon) or dynamic materials whose dielectric constant varies as a function of external forces (e.g. electro-optic polymers).

Equations defining the momentum of the plasmon wave and the wavelength-, angle-, and phase-dependence of such systems are well described for Kretschmann as well as GCSPR instrumentation. Interested readers are encouraged to reference the comprehensive review edited by Jiří Homola for additional information about SPR fundamentals.[5] The same basic equations hold true for EOSPR.

BRIEF DESCRIPTION OF THE INVENTION

SPR-enhanced photocatalytic systems with accompanying optical schemes for maximizing broadband coupling into said systems are described herein. Key steps defining the proposed approach to efficient conversion of incident light energy to photocatalytic activity are the following:

1. Angular dispersion of incident light onto an SPR-active surface, so that each incident wavelength will strike the surface at a range of angles and relative intensities that approximate the resonance curve (i.e. plot of intensity vs. angle) for said wavelength.
2. Coupling of this light to one or more angle-dependent SPR-active interfaces between appropriate metals and dielectrics. Presented herein are various GCSPR, Kretschmann, and EOSPR coupling schemes.
3. Transfer of photonic energy from the excited plasmon to one or more materials with photocatalytic activity, uniformly coated or patterned, and adjacent to the SPR-active surface. This transfer of energy may occur directly, via sensitizers, because of local enhancements of the surface electric field, and/or by generating hot electrons.
4. Materials at the catalytic interface may be chemically functionalized to facilitate specific reactions (e.g. adding hydroxyl groups to change the local pH).
5. The optional enclosure of the photocatalytic system in a fluid-tight apparatus where fresh reagents actively or passively circulate over the catalytic surface(s) (e.g. water pumped across the surface) and products are easily extracted (e.g. evolution of $H_2$ gas from aqueous solution via semi-permeable membrane). Embodiments designed to be completely submerged are also described.
6. The optional arrangement of these individual SPR-active photocatalyst constructs and/or associated optical components into one-, two-, or three-dimensional arrays.
7. The optional integration of the photocatalytic system(s) with established techniques for concentrating incident light, and/or tracking moving light sources.
8. The optional inclusion of feedback mechanisms that monitor the efficiency of resonant coupling, photocurrent generation, or photocatalytic efficiency, and use this data to affect physical changes that optimize catalytic activity.

The potential value of each of the proposed elements of the photocatalytic system is discussed. Various embodiments and accompanying applications are suggested. One supporting experiment that demonstrates proof-of-principle plasmonic enhancement of a GCSPR system is described.

Embodiments are described incorporating alternative arrangements of the basic constituent parts of the disclosed photocatalytic surface. Every possible combination of alternatives cannot be disclosed in a patent application of reasonable length and clarity, so representative examples are used to illustrate how alternative materials, manufacturing techniques and methods of operation can produce enhanced photocatalysis. It will be apparent that specific alternatives and combinations not disclosed will produce enhancements relevant to different sources of illumination, operating environments and chemical reactions. Each of the disclosed variables, manufacturing methods, materials, and operating methods can be applied individually or in combination with one or more of the other disclosed variables, manufacturing methods and operating methods to provide enhanced photocatalysis according to the disclosure.

BRIEF DESCRIPTION OF THE DRAWINGS

FIG. 2 is a schematic drawing showing two views of one possible architecture for a GCSPR photocatalytic surface;

FIG. 3 is a schematic drawing that illustrates one possible patterning scheme for two photocatalysts and one sensitizer on a single GCSPR surface;

FIG. 4 demonstrates an alternative GCSPR configuration with a two-dimensional grating; half of this structure is patterned with photocatalyst for illustrative purposes;

FIG. 7 is a schematic drawing that illustrates one possible architecture for a GCSPR photocatalytic flow cell and an effective means of gathering polychromatic light energy and coupling said energy into a surface plasmon; this figure also shows one integrated scheme for separating reactants and products;

FIG. 8 is a second schematic drawing that illustrates a distinct architecture for a GCSPR photocatalytic flow cell. This second approach gathers polychromatic light energy and couples said energy into a surface plasmon by passing the light through a transparent substrate;

FIG. 9 is a third schematic drawing for a GCSPR photocatalytic system, which is designed for direct immersion into a liquid. This embodiment is made from several of the same components as the construct in FIG. 8 without the flow cell. Once again, the SPR-enhanced catalysis occurs at the SPR-active metal surface, but no flow cell is present so catalysis occurs in an unregulated fashion. The prism material may be selected to permit effective gathering of polychromatic light energy while the entire apparatus is submerged below a liquid (not shown);

FIG. 10 is a schematic drawing showing one possible architecture for a photocatalytic flow cell based on the Kretschmann configuration and an effective means of gathering polychromatic light energy and coupling said energy into a surface plasmon;

FIG. 11 is a schematic drawing showing one possible relationship between dispersive optics and a plurality of GCSPR surfaces, which suggests one possible architecture for a three-dimensional array of SPR-active photocatalytic systems;

DETAILED DESCRIPTION OF THE INVENTION

Figure 1:
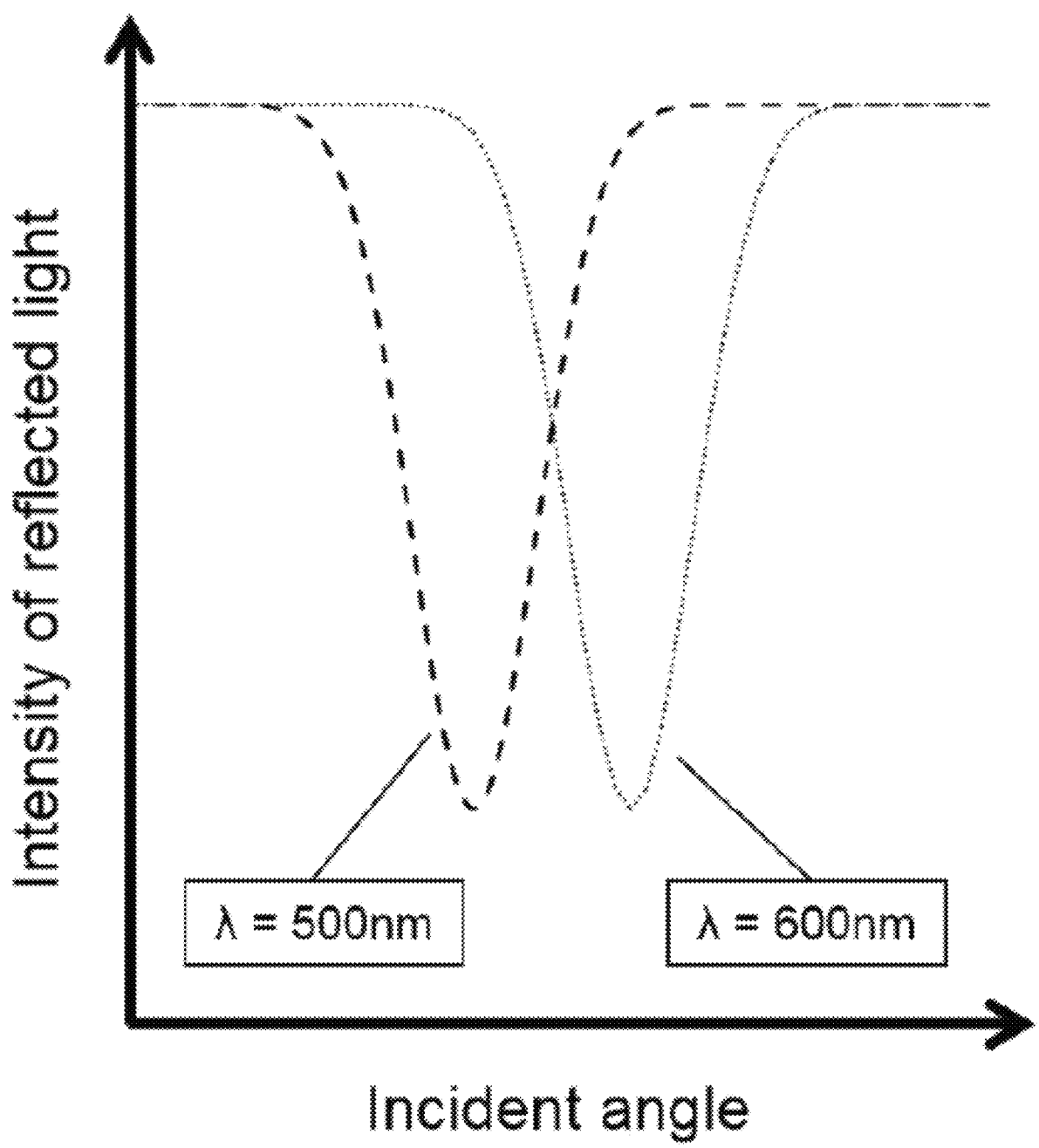
FIG. 1 is a graph that represents the angle- and wavelength-dependence of surface plasmon resonant coupling as is observed in Kretschmann, GCSPR, and EOSPR platforms.

As used herein, SPR stands for Surface Plasmon Resonance, GCSPR stands for Grating-Coupled Surface Plasmon Resonance, LSPR stands for Localized Surface Plasmon Resonance, and EOSPR stands for Electro-Optic Grating-Coupled Surface Plasmon Resonance. Angle measurements are primarily discussed in millidegrees (mdeg), where 1 mdeg=0.001 degrees. The term "adjacent" and its grammatical derivatives are used here to suggest a functional relationship between two objects that includes either direct physical contact or a separation by a sufficiently insignificant layer or set of layers such that the desired relationship between the two objects can proceed effectively unhindered, despite physical separation. At minimum, a "photocatalyst" is a material that accelerates chemical reactions in the presence of light. For the purposes of this discussion, one photocatalyst may be considered distinct from a second photocatalyst when the two materials differ in chemical composition (e.g. $TiO_2$ vs. $PbCrO_4$), deposition geometry (e.g. $TiO_2$ nanoparticles vs. thin films vs. bulk crystalline $TiO_2$), spatial location, or internal crystalline geometry (e.g. rutile vs. anatase $TiO_2$). These criteria are not exclusive; an additional distinction between two photocatalysts is their "excitation energy." The excitation energy of a photocatalyst refers herein to the set of photon energies that said photocatalyst can absorb and use for practical chemical work. These spectra are often complex, absorbing multiple wavelengths of light, but for the ease of the ensuing discussion, "excitation energies" will be discussed as single excitation maxima (e.g. 500 nm). The "resonant angle" of a given architecture will be referred to with a single value (e.g. 45 mdeg) for ease of discussion, however this term is used herein to refer to the range of incident angles where SPR may be practically achieved (e.g. 45±15 mdeg). A "resonance curve" refers to the set of angles and wavelengths that achieve resonance on a given system. Resonance curves for two wavelengths are shown schematically in FIG. 1. "Angle-dependent SPR-active surfaces" are surfaces where achieving SPR requires control of the incident angle; this term describes some approaches to the Kretschmann Configuration, GCSPR, and EOSPR, but is defined in contrast to angle-independent LSPR surfaces.

Described herein is a device with at least one angle-dependent SPR-active surface, one photocatalyst, and one complementary optical scheme that maximizes broadband coupling into at least one surface plasmon mode. Energy transferred to the plasmon mode is subsequently employed to enable photocatalytic applications. An angle-dependent SPR-active surface is required to realize the proposed broad-spectrum coupling. Constructs based on GCSPR, Kretschmann, and EOSPR are presented. The primary discussion of these technologies will focus on embodiments based on GCSPR. Differences inherent to the Kretschmann and EOSPR platforms will be elucidated as appropriate.

A discussion of the optical requirements for the proposed wavelength-dependent broadband coupling schemes based on angular-dispersion follows the discussion of the proposed SPR-active architectures. In these embodiments, incident light will pass through an object that generates angular dispersion on its way to the SPR-active surface, so that each wavelength strikes the surface at a slightly different angle. The identity, position, and optical properties of the components will be selected so that each incident wavelength is at the angle of optimal surface plasmon resonance. As can be seen in FIG. 1, while SPR resonance curves are centered around a particular wavelength, they have a non-trivial width. This suggests that optimal energy transfer actually occurs when each wavelength strikes the surface over a small range of angles centered at its SPR minimum. Maximal efficiency is expected when the dispersion of the incoming light is tuned to precisely match the relative intensities and range of angles that define the dispersion of the surface plasmon. The width of this resonant peak represents another opportunity for proper selection of optical components, which could further improve plasmon excitation and photocatalytic activity.

Each of the SPR-active photocatalytic surfaces may exist in isolation, or in one-, two-, or three-dimensional arrays. Specific embodiments that illustrate some potential geometries of these arrays are presented below. In addition, individual photocatalytic surfaces may integrate into a fluid-tight system that drives reagents over the surface and/or removes products. In this way, the SPR-active surface, photocatalytic constructs, arrays of optical components, and tools for reagent handling may be assembled into a complete catalytic construct. Catalytic surfaces and/or derivative constructs may be incorporated into established solar technologies such as trackers and concentrators. Feedback mechanisms that monitor absolute reflected intensity, relative reflected intensity (e.g. comparing regions with and without diffraction gratings), reactant or product concentrations, and/or photocurrent generation may be employed to monitor the efficiency of resonant coupling and drive electronic or mechanical processes that optimize collection of light energy.

The role for sensitizers and chemical functionalization is briefly discussed below, but these are expected to parallel equivalent roles in established LSPR or non-plasmonic applications. Deposition and functionalization schemes for photocatalysts and sensitizers are also expected to resemble equivalent processes on non-plasmonic substrates.

The one-dimensional grating-coupled approach to SPR-enhanced photocatalysis is emphasized in this discussion. Surfaces that generate SPR using the Kretschmann configuration, 2D-GCSPR, and/or EOSPR are described in contrast to this fundamental approach to GCSPR. Each of these schemes takes advantage of the angle-dependence that LSPR systems mitigate. Unlike LSPR, the proposed approaches capture a large portion of the solar spectrum in a single plasmon mode. This mode is addressed by adjusting the angle incident on the plasmonic surface as a function of incident wavelength, and the resultant broadband approach to coupling is permitted by incorporating dispersive optical elements.

One example of a photocatalytic surface of the GCSPR-type includes: one diffraction grating, one SPR-active metal, one photocatalyst, and any necessary structural components that mechanically secure the surface for a given application. The basic element of the GCSPR photocatalytic surface is subject to many variations and enhancements as discussed below and can be incorporated to photocatalytic systems. The geometry and materials selected for the GCSPR surface may be optimized to excite surface plasmons and will serve as the substrate upon which photocatalytic materials are deposited and photocatalysis occurs. FIGS. 2A and 2B are side-sectional and top-plan views respectively, illustrating one embodiment of a GCSPR surface (20). Here, the underlying substrate (21) is made of silicon, lithographically patterned to contain a diffraction grating. This diffraction grating is shown as sinusoidal with a uniform pitch, but non-sinusoidal, blazed, and irregularly pitched gratings may prove advantageous in certain applications. An optional thin adhesion layer (22) makes the bond to the SPR-active metal (23) more robust. A uniform or patterned photocatalyst layer (24) is adjacent to the SPR-active metal, in direct contact or separated from the metal by a thin spacer layer (not shown). Chemical functionalization of the bare metal (23) or of the photocatalyst (24) may be preferable for some applications, and FIG. 2 demonstrates a GCSPR system where two compounds (25, 26) are attached to a patterned photocatalyst in a 1:1 stoichiometric ratio. Simpler or more complex systems can be produced, as each layer of the proposed surface can either be doped or chemically functionalized to improve catalytic efficiency. As an example, organic compounds can be covalently attached to bare metal (23) to modify the local pH adjacent to the surface without affecting the functional groups that provide photocatalytic activity (i.e. 24). Other embodiments may incorporate natural or synthetic enzymes/ribozymes (not shown) that are adjacent to the inorganic catalysts. Sensitizing molecules (not shown) can likewise be added to the system, gathering light from select solar wavelengths and transferring this energy into the photocatalyst. As with chemical functionalization, sensitizers could be located at nearly any position within the proposed construct. Examples include covalent attachment of a sensitizer to a catalytic oxide (24) or mechanical immobilization of a dye molecule in an underlying polymer (not shown).

A second manufacturing scheme for a GCSPR surface builds from a planar structural surface with a diffraction grating embossed (or otherwise patterned) into an adjacent polymer layer. The complete set of steps defining this alternative approach are not illustrated here, but this proposed structure aims to reveal how many distinct sets of manufacturing steps may produce a functionally equivalent surface. In this case, the surface with the added diffraction grating could be covered with an appropriate adhesion layer (22), an SPR-active metal (23), photocatalysts (24), sensitizers, and chemical functionalization (25, 26) as above. At this point, the described structure would functionally resemble the full construct (20) illustrated in FIG. 2.

FIG. 3 represents one of myriad deposition schemes for catalysts and sensitizers on a GCSPR surface (30). In this arrangement, the SPR-active metal surface (31) is patterned with two distinct photocatalysts (32, 33) as well as a sensitizer (34). Varying sizes, shapes, and stoichiometric ratios can be employed, and this diagram illustrates a 1:2:3 ratio between sensitizer and two different catalytic particles. This image deliberately lacks further surface modifications for the sake of clarity, but the approaches to additional functionalization of such a system would mirror those described above. An analogous image for a Kretschmann-based surface would appear nearly identical, but the ruled lines of the schematic would be absent to suggest the planar, prism-based configuration.

Numerous useful photocatalysts exist, including binary semiconductors ($TiO_2$, CdS), ternary semiconductors ($PbCrO_4$, $SrZrO_3$), quaternary semiconductors ($Cu_2ZnSnS_4$, $Bi_2AlVO_7$), and any other material that improves catalytic efficiency in the presence of incident light. This efficiency can be further honed by incorporating sensitizing compounds such as organic dyes (Rhodamine B), inorganic dyes (various ruthenium(II) complexes), quantum dots (CdS), polymers (colloidal $IrO_2$), and naturally produced biological molecules (hypocrellin B).

An alternate embodiment of the GCSPR surface is shown in FIG. 4. This illustrates a top-down view of an SPR-active surface patterned with two orthogonal diffraction gratings (40). A dashed line divides the upper-left region with bare gratings (41) from the lower-right region that illustrates gratings with several deposits of photocatalyst (42). In the illustrated embodiment, each of the two diffraction gratings has a distinct pitch (43, 44). Approaches to construction of these two-dimensional GCSPR surfaces is otherwise identical to the one-dimensional fabrication steps already outlined. The same diverse set of catalysts, sensitizers, and functionalizations may be employed.

In this geometry, incident light of both S- and P-polarizations contribute to the excitation of a plasmon, and therefore to the overall catalytic efficiency. Two gratings with differing pitches may also prove advantageous by enhancing more than one concurrent reaction, such as the simultaneous reduction and oxidation of chemical species, or by permitting plasmonic enhancement of two sequential catalytic steps in a multi-step process. Specific circumstances may arise where the benefits of a two-dimensional grating exist even when the two grating pitches are identical (not shown). Due to the angle and polarization requirements for coupling into each grating, the overall degree of coupling in the two-dimensional system will be reduced in one of the dimensions unless additional optical hardware separates the two polarizations into distinct optical pathways. A simple, inexpensive compromise may precisely optimize broadband light coupling for the P-polarization as described for one-dimensional GCSPR, but position the surface at a small tilt so that S-polarized light strikes the surface at a reasonable angle to achieve some resonance using this second grating.

Figure 5:
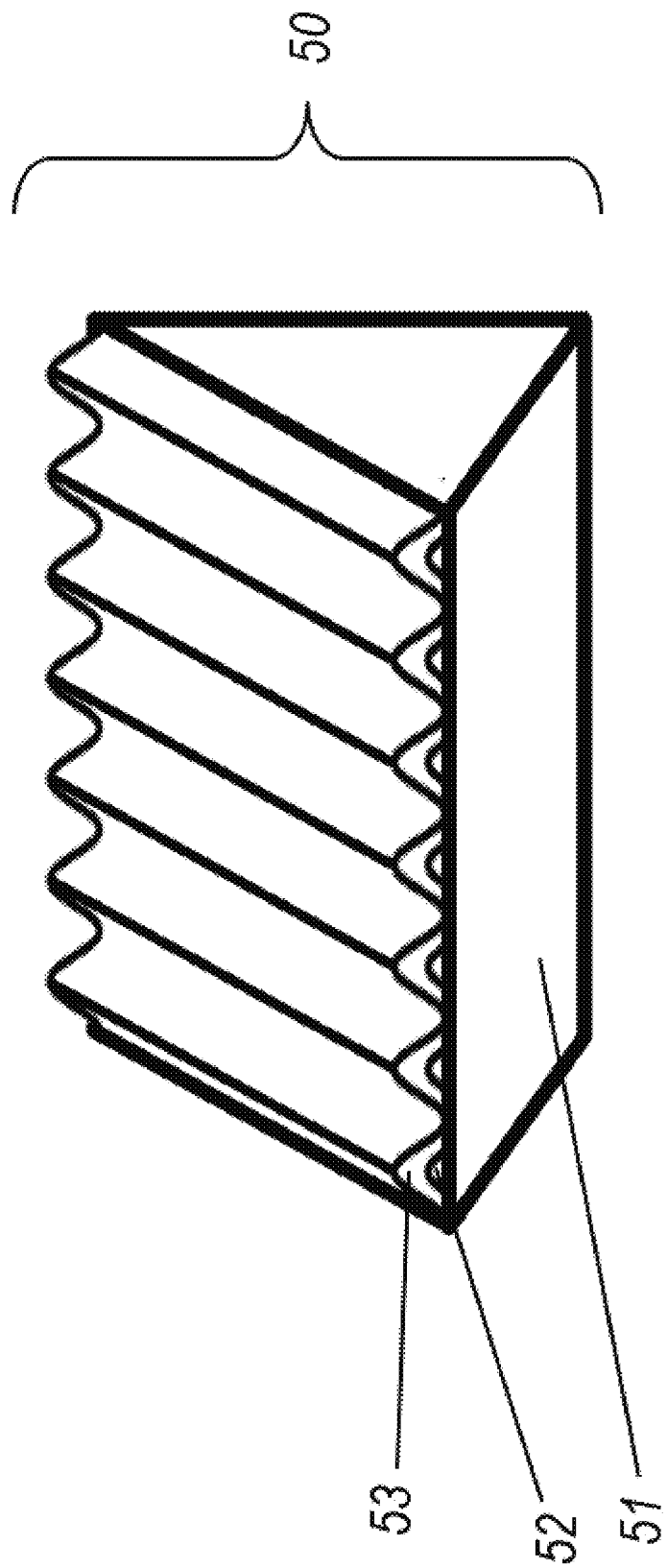
FIG. 5 demonstrates an alternative approach for two-dimensional coupling into a hybrid GCSPR/Kretschmann configuration.

The concept of an orthogonal grating used to capture additional energy into a plasmon mode also suggests a hybrid GCSPR/Kretschmann system (50) as shown in FIG. 5. One embodiment will have a grating structure (51) etched into or otherwise constructed on one surface of a prism (52). Here, an underlying grating structure is built with a polymer whose refractive index matches that of the prism (i.e., 51 and 52 have matching dielectric constants). A thin layer of SPR-active metal (53) permits P-polarized coupling at the prism-metal interface (i.e. the Kretschmann configuration) and S-polarized coupling via interaction with the grating structure (i.e. GCSPR). Depending on the application, light may strike the grating through any face of the prism. Grating-coupled excitation may likewise occur with incident light striking the opposite side of the metal surface as the prism. Arrays built from these hybrid optical elements may be constructed from inexpensive materials and printed in rigid or flexible sheets. Alternative embodiments may use a disposable GCSPR component positioned orthogonally to a prism. This arrangement would likely require an index matching fluid, but may be desirable in select circumstances.

Figure 6A:
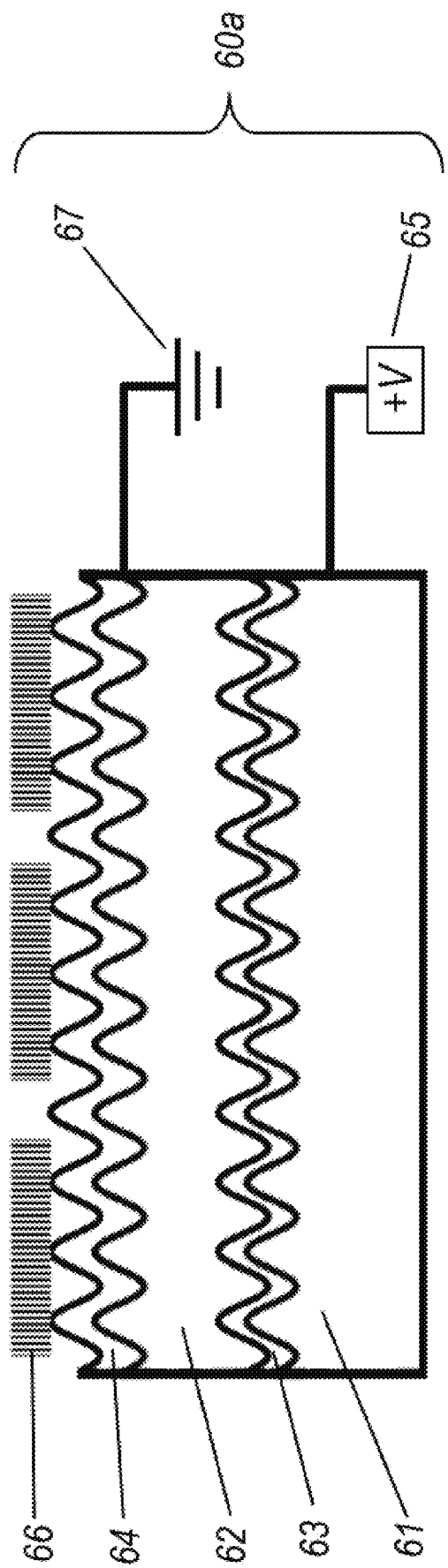
FIG. 6 is a schematic drawing that illustrates three distinct approaches to the EOSPR photocatalysis scheme.

An extension of the GCSPR platform, Ciencia's electro-optic grating-coupled approach to surface plasmon resonance (EOSPR) is a novel approach to tailoring the resonant conditions at an SPR-active surface without requiring moving parts. FIG. 6A illustrates one embodiment of an EOSPR photocatalytic surface (60a). Here the surface is built atop a rigid substrate (61). In this structure, the substrate material will be conductive (e.g. doped silicon) and will be in electrical contact with a voltage generator (65). This embodiment positions the diffraction grating in the underlying substrate (61), and a material displaying significant electro-optic activity (62) is deposited atop this structure. An adhesion layer (63) between the substrate and the electro-optic material may enhance adhesion. The SPR-active metal (64) is adjacent to the electro-optic material and is also in electrical contact with a voltage generator (65), so that an electrical potential can be generated across the electro-optic material (62). An adhesion layer between the electro-optic material and the SPR-active metal may also prove desirable, but is not shown in this figure. One or more patterned and functionalized photocatalysts (66) are positioned to receive energy from the excited plasmon mode. Sensitizers may again be employed. The illustration shows a positive voltage (65) applied to the underlying substrate, while the SPR-active metal (64) is kept at ground potential (67). This represents one of numerous ways that a bias can be established across an electro-optic component (62). Both surfaces may be at a significant potential when compared to ground. Static or varying voltages applied across these two surfaces (61, 64) permit further tuning of resonant conditions. Rapid cycling of the voltage applied across this electro-optic material (62) would induce similarly rapid changes in the resonant conditions. In combination with a one- or two-dimensional grating architecture, such a system could facilitate redox reactions and/or efficiently catalyze several steps in a multi-part reaction.

Figure 6C:
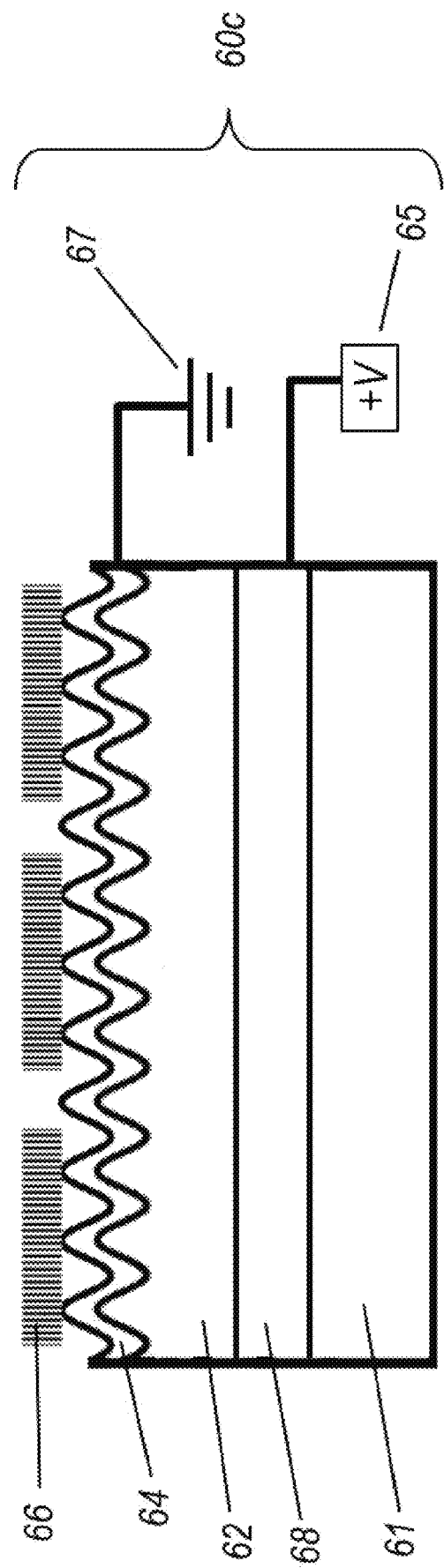

Additional approaches to EOSPR development are illustrated in FIGS. 6B and 6C. These proposed catalytic surfaces (60b and 60c, respectively) functionally resemble the construct from FIG. 6A, but represent distinct manufacturing schemes. FIG. 6B demonstrates a second embodiment (60b) that is built atop a planar substrate (61). Once more, this is a conductive material and is in electrical contact with a voltage source (65). The adhesion layers described for the construct of FIG. 6A are not illustrated in this architecture, but could be incorporated into any variant architecture as appropriate. In the embodiment of FIG. 6B, the grating pattern is produced directly in the EO layer (62). The surface metal (64) is at a set or variable potential, in this case fixed at the ground potential (67) and covered with photocatalysts (66), with or without sensitizers or additional chemical functionalization. FIG. 6C demonstrates a third embodiment (60c) that is built atop a non-conductive planar substrate (61). A thin conductive layer (68) is added in electrical contact with a voltage generator (65). The overlying EO material is once more patterned with a diffraction grating and sandwiched between the two conductive layers (64, 68). Once again, the surface metal (64) is illustrated to be fixed at ground potential (67) and covered with photocatalysts (66), with or without sensitizers or other chemical functionalization (not shown). These three figures aim to illustrate some potential manufacturing approaches for the development of the EOSPR surface, but are limited in scope and do not define the complete set of claimed manufacturing schemes.

An EOSPR-based approach offers several advantages. SPR-coupling conditions are exquisitely sensitive to amount of mass adjacent to the SPR-active surface. This sensitivity is desirable in some circumstances—it is the property that permits SPR biosensing—but it potentially complicates optimization of photocatalysis, as the varying presence of reactants or products at the surface may change the local environment. The EOSPR platform would permit correction of any changes in the coupling conditions caused by accumulating material at the catalytic surface as a function of applied voltage. To illustrate, imagine that a particular EOSPR system was optimized to achieve resonance with a bare catalytic surface. Addition of reagents would move the system out of resonance. Applying voltage across the underlying electro-optic material would change that material's dielectric constant and return the system to resonance. An incorporated feedback mechanism would continuously monitor whether the system is at resonance, and automatically adjust the applied voltage to maximize catalytic efficiency. In one specific embodiment, a graphene layer would measure and optimize the photocurrent generated at the surface, which in turn would automatically adjust the applied voltage across the EO material to maximize photocurrent. A second embodiment would optimize coupling as a function of the measured reflectivity of light from the SPR active surface. Changes in the resonant conditions would once more arise by adjusting the applied voltage. Such control schemes could be hardwired, computer controlled, or require manual input.

In other EOSPR-based designs, adjustment of the voltage applied across the polymer layer could alter the energy of the excited surface plasmon. Such variation of the resonant conditions could potentially permit selective outcoupling to one of several different photocatalytic materials or sensitizers. This would enable optimization of multiple steps in a complex chemical reaction. With EOSPR, these changes can occur rapidly, without altering the properties of the incident light. While voltage may cycle, no current will flow across the surface, suggesting considerable catalytic utility with minimal power consumption.

Finally, since the temperature of the SPR-active surface also affects the resonant conditions, EOSPR represents one possible scheme for counteracting the effect of surface temperature fluctuations. Once more, these changes to the resonant conditions can be compensated by the application of voltage across the surface. Other techniques for heating and cooling may be employed, further optimizing overall catalytic efficiency. Example schemes include the integration of resistive heating elements into the SPR-active surface which could be controlled with a digital thermometer and a feedback loop. Similarly, in direct sunlight or other high-powered light sources, temperature control may be achieved by conversion of incident light to heat (e.g. absorption of light with an adjacent black surface). Slight temperature fluctuations at the surface could also be accommodated by modifying the surface angle with respect to the sun or by adjusting the flow rate of the reagents through the flow cell.

Achieving the optimal photocatalytic activity requires not only the above-described SPR-active surfaces, but a complementary optical scheme. The following paragraphs outline several possible optical paths, with an emphasis on a set of approaches that enable highly-efficient broadband transfer of light into a surface plasmon. The proposed schemes aim to overcome the fact that photocatalysts have a single excitation wavelength. While a photocatalyst may only absorb select wavelengths, this limitation does not affect the plasmon in a GCSPR, EOSPR, or Kretschmann platform. Here, the plasmon can absorb light from nearly any wavelength as long as each strikes the surface at the appropriate angle. If resonance has been achieved and all else is held constant, changes in the incident wavelength of monochromatic light can be accommodated simply by adjusting the incident angle. This suggests a system where individual wavelengths from a polychromatic light source strike an SPR-active surface at different angles, each of which is the SPR angle for said angle and said system. Dispersive optics, such as a prism, transmission grating, or Fresnel prism, could be employed to slightly alter the angle of each color present in collimated white light. Dispersion of light onto these surfaces permits multi-wavelength excitation of the photocatalyst by first transferring this energy to a plasmon. In these proposed embodiments, the plasmonically active surface effectively acts as a funnel of the broadband incident energy into a single plasmon mode. Subsequent transfer of this full-spectrum energy to the photocatalyst contributes to overall photocatalytic activity.

The possibility of broad-spectrum collection of light energy suggests many useful solar applications. The most efficient coupling of incident light into a surface plasmon mode requires that the light is collimated and P-polarized, and then strikes the surface with precise combinations of wavelength and angle. However, sunlight is approximately collimated and while S-polarized light does not couple into the plasmon, it does contribute toward the overall activity of any sunlight-stable photocatalytic reaction due simply to increased irradiance. This suggests an optical scheme to achieve resonance with solar energy that requires neither collimating lenses nor polarizers. In fact, for sunlight-driven SPR-enhanced photocatalysis, only two components are required: the SPR-active surface and a structure for precise angular dispersion, such as a Fresnel prism, transmission grating, or prism.

While a single metal-coated prism represents the minimum optical component required for the proposed approach to resonance, additional elements may prove preferable for certain applications. As mentioned above, the most efficient energy transfer occurs when each wavelength strikes the surface over the small range of incident angles that match the inherent dispersion of the plasmon mode (see FIG. 1). Although sunlight is nearly collimated, additional lenses may improve the collimation and thus the match between dispersed sunlight and the range of energies and angles that excite the plasmon. Similar schemes may also be beneficial when attempting to couple non-solar energy to an equivalent system. Lenses and mirrors external to the proposed photocatalytic system may act to collect, concentrate, and/or collimate incident light. Additional schemes for maximizing energy transfer to the plasmon could include birefringent materials that separate incident light as a function of polarization, permitting P-polarized light to interact as above, while redirecting and rotating the S component so that it too achieves resonance.

Specific optical embodiments and approaches to establishing an effective interface with the photocatalytic surface are described below. In many of these embodiments, the dispersive optics and the SPR-active photocatalytic surfaces are assembled in one-, two-, or three-dimensional arrays. One approach to fabrication builds the catalytic surfaces and optical elements as "sheets," facilitating large-scale and low-cost manufacturing. The described structures could be incorporated into one or more fluid-tight chambers, which would permit active or passive flow of reagents across the photocatalytic surface. One such design is illustrated in FIG. 7.

FIG. 7 details a construct (70) that includes incident light (71), an array of prisms (72) and collimating lenses (73), an SPR-active photocatalytic surface (e.g. 20), fluidics (74, 75), an integrated sample collection scheme (76, 77), and additional structural components necessary to build a fluid-tight "flow cell." A pump to mechanically drive the fluid may be included, but is not shown in this embodiment. With appropriately designed SPR-active surfaces and properly selected prisms, each incident wavelength would strike the GCSPR surface at the range of angles that maximizes SPR. This energy would be transferred to one or more photocatalysts or sensitizers (not shown), ultimately increasing the efficiency of the desired reaction. In this diagram, fresh reagents enter from the left (74), flow across the surface plasmon-enhanced catalytic surface (20), and are converted to products. Unused reagents continue through the fluid outlet (75), while products pass through a semi-permeable membrane (76) and toward a collection chamber (77). Flow could be actively driven by pumps or passively driven by physical phenomena (e.g. thermal expansion, capillary action, osmotic gradients). Additional tubing and valves could permit reagent recirculation and/or the subsequent introduction of other reagents that facilitate secondary, tertiary, or higher-order synthetic steps. Catalytic systems built from Kretschmann arrays, EOSPR, or two-dimensional GCSPR surfaces would resemble this architecture.

FIG. 8 details an alternative embodiment (80), where the optical array (e.g. 83, 84) would be adjacent to the underlying substrate and incident light (85) would excite the plasmon from "beneath" the photocatalytic surface (e.g. 20). A fluid-tight enclosure (81) and fluidics (82, 86) would provide control over flow rates. Photocatalysts, sensitizers, and chemical functionalizations are not shown for clarity. Such an arrangement may permit the manufacture of a cistern with a transparent underlying substrate and optics positioned so that external solar irradiance catalyzes water-treatment reactions within the chamber. With the correct photocatalyst, such a system could provide inexpensive access to clean drinking water.

It is noteworthy that although this discussion primarily focuses on SPR-based enhancements to photocatalytic efficiency, many of the proposed embodiments will also support non-plasmonic activation. This additional enhancement of the reaction rate occurs when energy is transferred to the photocatalyst by direct illumination, adding to bulk catalytic activity. This is desirable in many circumstances, but in some cases, reactants, catalysts, products or byproducts may be unstable in direct sunlight. With these compounds, conversion of light energy to a plasmon without direct illumination of the reaction vessel may be preferable. FIG. 8 represents one such embodiment, where the surface geometry promotes catalytic activity via a surface plasmon, but allows minimal direct excitation or stray light to reach the catalytic surface.

In any geometry, arranging the optical and catalytic components to form a flow cell has several advantages. A mechanical pump can help establish precise control over reagent flow rates and surface temperatures. In addition, passing a fluid through tubing adds a barrier that isolates the end-user from potentially toxic reagents, catalysts, or products. Finally, fluid-tight connections in a photocatalytic system would prevent reactants or products from leaving the system. Such a design could be advantageous when integrated with energy-generating technologies, such as a hydrogen fuel cell. In one envisioned embodiment, water flows over an SPR-active surface and is photocatalytically converted to $H_2$ and $O_2$ while light is abundant. After the sun sets, in inclement weather, or when it becomes desirable to retrieve the stored energy, an integrated fuel cell could generate useable electricity. This may occur simply by driving the photocatalyzed reaction in reverse. Because the system is closed, it could be filled once with water and then undergo many charging and discharging cycles, without wasting this precious resource. Such a design may have particular value in desert climates.

Despite the aforementioned benefits of a closed system, the optical components and the photocatalytic surfaces can operate equally well in an environment that is not fluid-tight. In fact, an SPR-active photocatalytic construct can be designed to operate while completely submerged in a fluid. FIG. 9 represents one such embodiment, which is built from optical and catalytic components extracted from FIG. 8, but eliminates the flow cell. Specifically, this embodiment (90) illustrates an optical array (91, 92) that is adjacent to the photocatalytic surface (20). Once more, the incident light (93) excites the plasmon from "beneath" the photocatalytic surface (20). Photocatalysts, sensitizers, and chemical functionalizations are not shown for clarity. Immersing this construct (90) could permit SPR-enhanced photocatalytic activity to occur directly in a body of water (not shown). In this case, the geometry and/or material of the dispersive optics may need to change to accommodate the difference in refractive index between water and air.

FIG. 10 details an alternative embodiment (100), with a simplified optical array containing prisms (104) that have been coated with a thin layer of an SPR-active metal (103). This Kretschmann-based SPR-active prism-metal array could be manufactured in large quantities at low cost. Angle-based dispersion of the incident light (105) into component wavelengths that strike the prism-metal interface at approximately the SPR angle permits broadband coupling into the plasmon mode. Photocatalysts are not shown in this diagram, but would be located at the fluid-metal interface as illustrated, and this greatly simplified approach to SPR coupling and photocatalysis would be amenable to mass production. As above, a fluid-tight enclosure (101) and fluidics (102, 106) would provide control over flow rates, but are not strictly necessary. The benefits and limitations of including a flow cell in a GCSPR platform are discussed above, and parallel justifications are appropriate for the Kretschmann configuration.

FIG. 11 illustrates a relationship between an underlying substrate (111), an SPR-active grating (112), and dispersive optical elements (113). This image shows several GCSPR surfaces in an array, and such a geometry could be extended in all three dimensions. The optical components may also be positioned in a two-dimensional array. The dispersive optics are shown here as a prism (113), but other components such as transmission gratings and Fresnel prism may be employed. Although a one-dimensional GCSPR surfaces is illustrated, two-dimensional gratings and/or EOSPR surfaces may be similarly arranged. This particular embodiment of FIG. 11 shows the prism (113) and the photocatalytic surfaces (111, 112) forming a right angle, but different relative positions of these components may be employed to achieve optimal coupling for a particular application. Indeed, it may be preferable to mount the optical components and the photocatalytic surfaces on hinged structural elements that permit a variable relationship between these structures.

Figure 12:
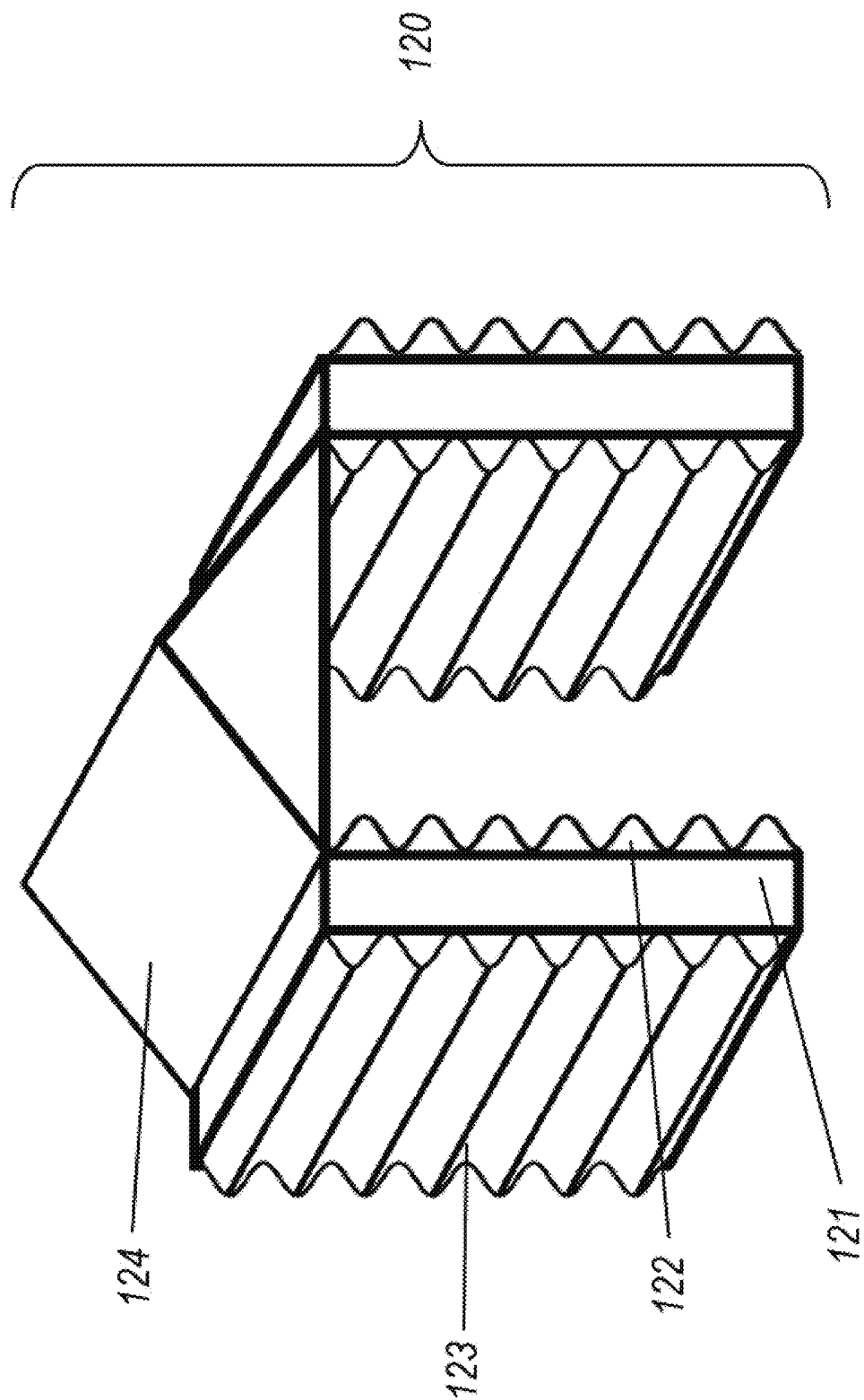
FIG. 12 is an alternate embodiment of a three-dimensional GCSPR-based photocatalytic array.

FIG. 12 illustrates an alternative relationship between the underlying substrate (121), two SPR-active gratings (122, 123), and dispersive optics (124). Once more, this image shows several GCSPR surfaces in an array, with a geometry that can be extended to fill all three dimensions. An accompanying two-dimensional array of optical components may also be explored. Like the embodiment in FIG. 11, the dispersive optics are shown as a prism (124), but other components, such as transmission gratings and Fresnel prism, may be employed. Two-dimensional gratings and/or EOSPR surfaces may replace the one-dimensional GCSPR surfaces. In addition, the angle between these components will vary to achieve optimal coupling.

Figure 13:
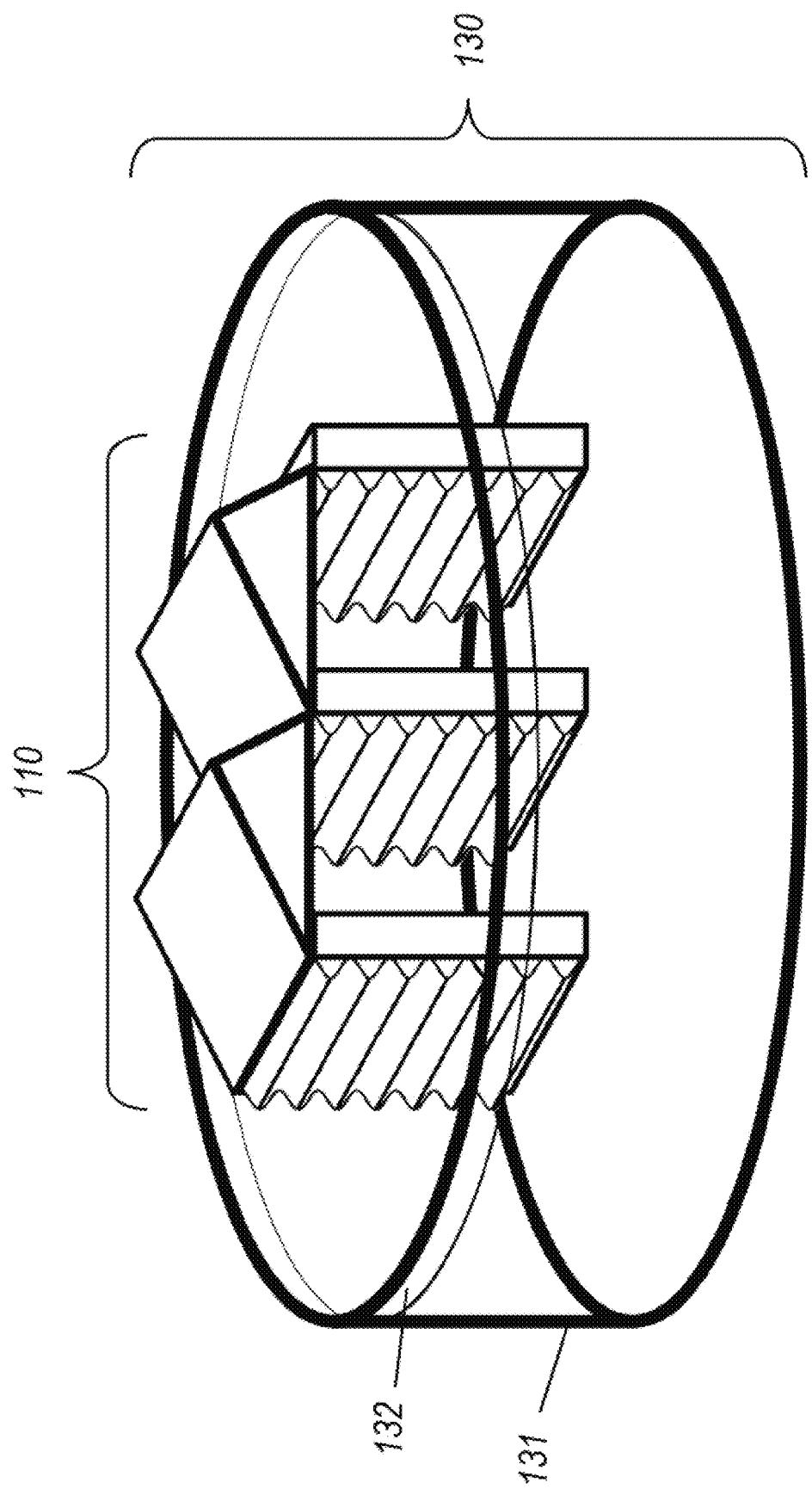
FIG. 13 illustrates an approach to utilizing the construct of FIG. 11 by immersing the catalytic surfaces in a container of liquid.

FIG. 13 submerges one portion of the construct from FIG. 11 into a fluid. This multi-layered approach to GCSPR that utilizes oblique illumination represents another scheme for maximizing reaction efficiency (130). An array of SPR-active surfaces (110) is immersed in a container (131) that is filled with a liquid (132). Immersion of these photocatalytic surfaces into the liquid permits abundant direct contact between the photocatalytic surface and a liquid reagent. The increased photocatalytic surface area facilitates slow reactions in the presence of a saturating light source. Such a system can integrate with technologies that optimize the incident angle flow liquid or gas reagents over this catalytic array. The platform would also benefit from adaptation of established techniques for tracking incident light as well as isolating and capturing desired products.

Figure 14:
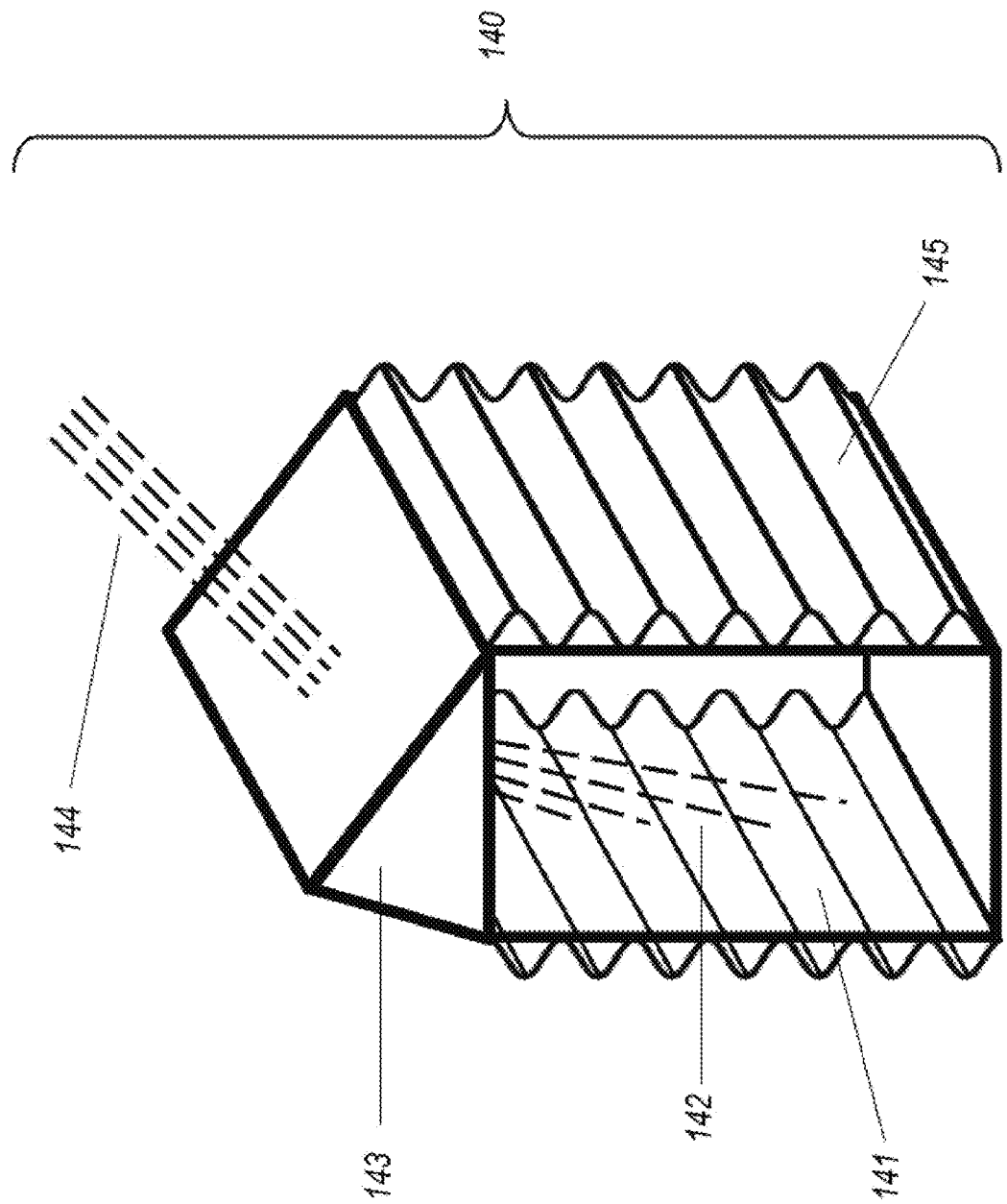
FIG. 14 shows one more alternate relationship between the dispersive optics and GCSPR-active photocatalytic surface. Here, incident light passes through the structural component supporting the grating and excites the plasmon from the opposite side of the metal as the photocatalyst.

FIG. 14 illustrates an alternative relationship between an optically transparent underlying substrate (142), two SPR-active gratings (141, 145), and dispersive optics (143). These components (140), taken together, could once more be arranged in an array format. In this geometry, the incident light (144) passes through the prism into the transparent support material (142). In this scheme, light strikes the "back" of a thin SPR-active grating (141) where it excites a plasmon. These surface plasmons then excite adjacent sensitizers and/or photocatalysts (not shown) and enhance catalytic activity. Advantages to this architecture include the fact that the proposed technique may permit photocatalytic reactions that use opaque reagents or photocatalysts, and/or generate opaque products. Derivative designs may permit photocatalytic reactions of compounds that are not stable in direct sunlight. Similar architectures could be built with two-dimensional GCSPR and EOSPR technologies.

Figure 15:
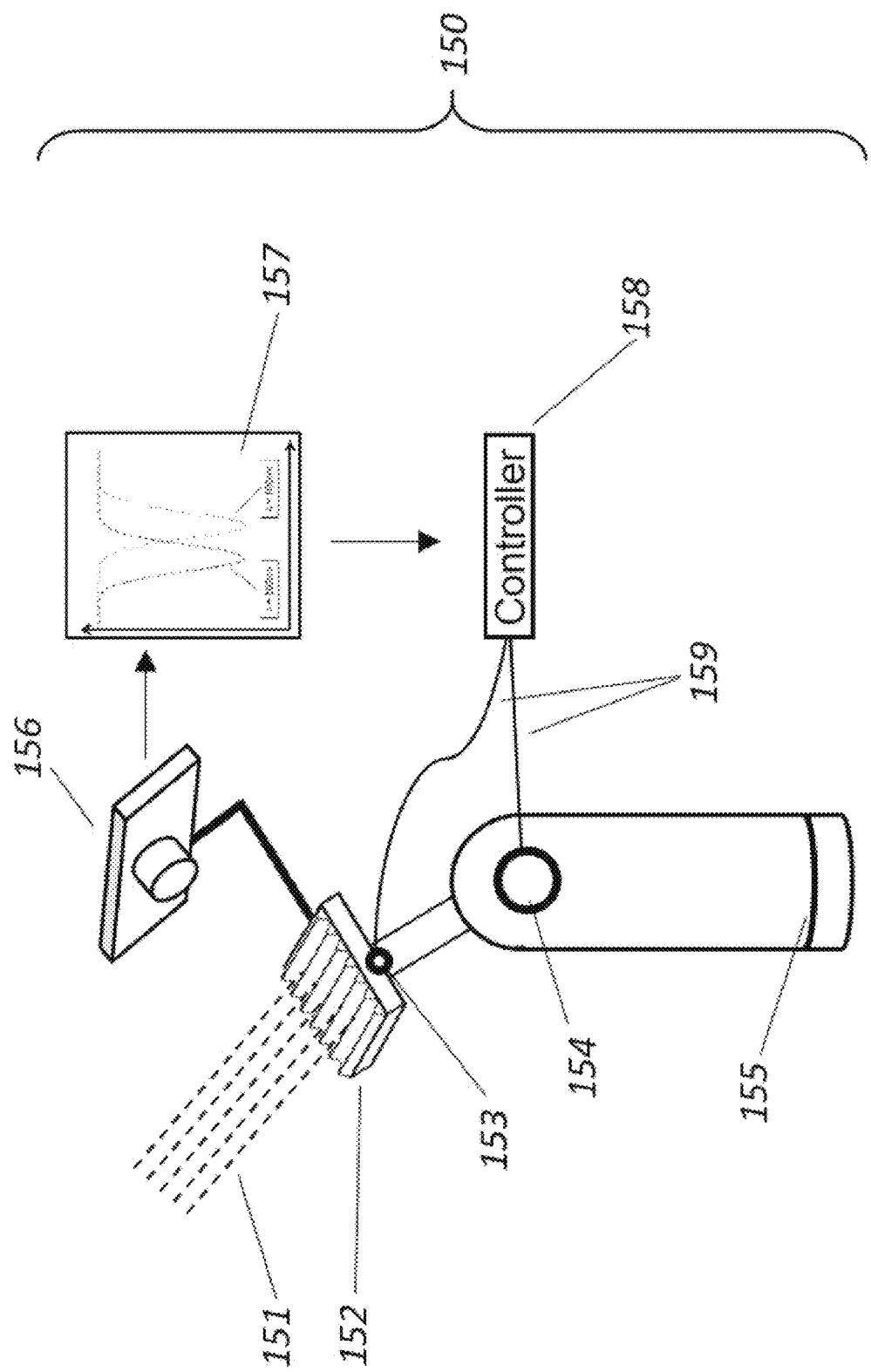
FIG. 15 shows a mechanical system that moves a GCSPR-active photocatalytic surface with respect to a stationary base. The illustrated feedback circuit permits automatic repositioning in response to data such as photocurrent generated and/or SPR efficiency.

FIG. 15 illustrates one possible mechanism for maintaining optimal resonant conditions using a feedback-driven mechanical positioning scheme (150). Here, changes in the direction of the incident light (151) relative to the GCSPR-active photocatalytic surface (152) may be accommodated. In this embodiment, a motor-driven pivot (153) positioned just below the photocatalytic surface (152) provides fine adjustments to optimize resonance. A motor so positioned could be selected to have millidegree precision across a narrow range of angles (e.g. this first motor could change the position of the surface by ±2 degrees, but in 1 mdeg increments). Coarse tracking of the sun could be achieved with a second motor positioned in the same axis (154). If this second motor permits 180 degrees of travel with 1 degree precision, the combination of the two motors should permit resonance at any position along the solar path. Additional flexibility for tracking a light source may include a motorized rotating base (155). In the illustrated embodiment, the intensity of light reflected of the SPR-active surface is recorded by a detector (156), and the interpretation of this data permits feedback for solar tracking applications. Tracking systems that monitor the intensity of incident light are well-described. The envisioned system (150) could permit a feedback circuit based on intensity, but it would also allow solar tracking to be a function of resonant coupling. Here, the detector (156) could simultaneously monitor two regions on the surface (152), comparing the intensity of light reflected off a grating-patterned SPR surface, to the light reflected off a planar surface that is otherwise identical. Optimal resonance efficiency may be defined by the minimum ratio of light intensity reflecting off the GCSPR surface vs. the planar control. Collimating optics and filters may be required but are not shown. Changes in the collected data (157) as a function of changes in the relative position of the surface (152) may be used to define a feedback circuit where the efficiency of SPR is used to track the sun. Light source tracking as depicted in FIG. 15 may be achieved using a controller (158), positioning controls (153, 154) and appropriate connections (159). Alternatively, the angle of the incident light may be adjusted. In a second embodiment, a rotating mirror (not shown) positioned within the incident path (151) changes the angle of the light striking the photocatalytic surface. Adjustments in the mirror position may accommodate changes in the resonant conditions. An additional possible embodiment eliminates the fine-tuning motor (153) and instead maintains resonance by adjusting the voltage applied across an EOSPR surface. Other approaches to maintaining resonance under variable conditions include manual positioning or mechanical deformation of optical components.

Unlike prior art, the approach proposed herein permits full-spectrum coupling of incident light energy into an inexpensive plasmonic system that supports innumerable potential photocatalytic reactions in a format that is amenable to large-scale manufacture. The platform could readily integrate with existing sample-handling systems by way of built-in fluidics. Applications for the above-described Kretschmann, GCSPR, and EOSPR photocatalytic systems include large- and small-scale systems of varied designs, all of which act to effectively convert light energy into the work driving desirable chemical reactions. Selected practical embodiments with broad potential impact include a combined apparatus for water splitting and $H_2$ utilization collection, self-cleaning materials, self-sterilizing materials, and tools for environmental monitoring and concurrent treatment. While only the aforementioned rigid and planar surfaces have been described in detail, alternate embodiments of the proposed photocatalytic systems could be built from curved, irregular, or flexible materials. While flexibility limits the theoretical catalytic efficiency, it enhances the set of potential applications. As an example, wearable photocatalytic devices could potentially charge personal electronic devices.

It should also be noted that unlike many other solar technologies, the approach to photocatalysis described herein is not necessarily hindered by elevated reaction temperatures or pressures. High-temperature and/or high-pressure systems may prove advantageous for select applications.

Experiments have demonstrated SPR-enhancement of photocurrent generation with modified versions of GCSPR biosensor chips. One such experimental platform measured photocurrent on a grating-patterned $Au/Al_2O_3$/graphene heterostructure as a function of incident angle and polarization. With P-polarized and collimated light at 633 nm, a dip in reflectivity was noted at approximately +/−10° from normal. The polarization was switched and the angle-dependent decrease in intensity disappeared, a confirmation of coupling with the surface plasmon. The photocurrent generated with P-polarized light striking at the resonant angle was found to be 4.6× the photocurrent generated at non-resonant angles with P-polarized light or any angle with S-polarized light. The magnitude of this enhancement is remarkable, considering that the system was optimized for biosensing and only one incident wavelength was employed. Full-spectrum coupling with optimized gratings and photocatalysts are expected to have profound improvements in catalytic efficiency.

NON-PATENT CITATIONS

1. Ameta R., Ameta S. C. Photocatalysis: Principles and applications. Crc Press. 2017.
2. Lan Y, Lu Y, Ren Z. Mini review on photocatalysis of titanium dioxide nanoparticles and their solar applications. Nano Energy. 2013; 2(5):1031-45. doi: https://doi.org/10.1016/j.nanoen.2013.04.002.
3. Willets K. A., Van Duyne R. P. Localized surface plasmon resonance spectroscopy and sensing. *Annu Rev Phys Chem.* 2007; 58:267-297.
4. Hou W., Cronin S. B. A review of surface plasmon resonance-enhanced photocatalysis. *Advanced Functional Materials.* 2013; 23(13):1612-1619. Doi: 10.1002/adfm.201202148.
5. Homola J. Surface plasmon resonance based sensors. *Physica-Verlag.* 2006.

PATENT CITATIONS

6. Page W., Gibson G. N., Guignon E. F., inventors; Ciencia Inc., assignee. Electro-optic Grating-coupled Surface Plasmon Resonance (EOSPR). U.S. Pat. Nos. 9,383,312 and 9,535,005.

The invention claimed is:

1. A photocatalytic system comprising:
a light source emitting light having a plurality of wavelengths;
photocatalytic surface comprising a diffraction grating; an SPR-active metal layer on said diffraction grating; and a photocatalytic material adjacent said SPR-active metal layer;
a dispersive optical system between said light source and said photocatalytic surface, said dispersive optical system separates said plurality of wavelengths and directs each said wavelength at said photocatalytic surface at a different incident angle; and
a dielectric material adjacent said photocatalytic surface
wherein light is diffracted at said diffraction grating and energy from said light is coupled to a surface plasmon formed at an interface of said SPR-active metal layer and said dielectric material, said surface plasmon providing activation energy for a chemical reaction enhanced by said photocatalytic material, and the incident angle for each said wavelength corresponds to an angle at which each said wavelength couples to said surface plasmon.

2. The photocatalytic system of claim 1, wherein said light source is the sun and said dispersive optical system separates sunlight into said plurality of wavelengths, said system comprising:
a substrate for said photocatalytic surface, said substrate having a fixed position relative to said dispersive optical system; and
a movable support arranged to alter an angular position of said dispersive optical system and photocatalytic surface to maintain a pre-determined angular orientation relative to the sun.

3. The photocatalytic system of claim 2, comprising:
sensors arranged to monitor resonant coupling of said light to said photocatalytic surface or photocatalytic efficiency and generate corresponding signals; and
a controller operatively connected to said sensors to receive said signals and alter the position of said movable support to improve said resonant coupling or said photocatalytic efficiency.

4. The photocatalytic system of claim 1, wherein said dielectric material is a fluid reagent, said photocatalytic system comprising:
a fluid circulation system arranged to circulate said fluid reagent over said photocatalytic surface; and
a reaction product collection system arranged to collect products of said chemical reaction.

5. The photocatalytic system of claim 4, wherein said chemical reaction is hydrolysis, said fluid reagent is water and said products are oxygen and hydrogen.

6. The photocatalytic system of claim 1, wherein said dielectric material comprises an electro-optic material, and said device comprises a controller configured to apply a variable electrical potential to said electro-optic material, said electro-optic material having an index of refraction that varies with the applied electrical potential and alters an angle at which each said wavelength couples to said surface plasmon.

7. The photocatalytic system of claim 1, wherein said dispersive optic is selected from the group consisting of a prism, a transmission grating, and a Fresnel lens.

* * * * *